US012667533B2

(12) United States Patent
Plitt et al.

(10) Patent No.: US 12,667,533 B2
(45) Date of Patent: Jun. 30, 2026

(54) ALDEHYDE-MODIFIED HYALURONIC ACID, METHOD FOR PREPARING SAME AND APPLICATIONS THEREOF

(71) Applicant: Merz Pharma GmbH & Co. KGaA, Frankfurt am Main (DE)

(72) Inventors: Patrick Plitt, Bad Homburg (DE); Colin Drabe, Frankfurt am Main (DE); Sibylle Mueller, Mainz (DE); Radovan Vukicevic, Frankfurt am Main (DE); Jens Neubauer, Glauburg (DE); Charlotte Reither, Bad Vilbel (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 735 days.

(21) Appl. No.: 17/415,044

(22) PCT Filed: Dec. 18, 2019

(86) PCT No.: PCT/EP2019/085829

§ 371 (c)(1),
(2) Date: Jun. 17, 2021

(87) PCT Pub. No.: WO2020/127407

PCT Pub. Date: Jun. 25, 2020

(65) Prior Publication Data

US 2022/0062151 A1 Mar. 3, 2022

(30) Foreign Application Priority Data

Dec. 19, 2018 (EP) .................................... 18214028
Aug. 9, 2019 (EP) .................................... 19191042

(51) Int. Cl.
*A61K 8/73* (2006.01)
*A61K 8/04* (2006.01)
*A61Q 19/08* (2006.01)

(52) U.S. Cl.
CPC .............. *A61K 8/735* (2013.01); *A61K 8/042* (2013.01); *A61Q 19/08* (2013.01); *A61K 2800/594* (2013.01); *A61K 2800/805* (2013.01); *A61K 2800/882* (2013.01); *A61K 2800/91* (2013.01); *A61K 2800/95* (2013.01)

(58) Field of Classification Search
None
See application file for complete search history.

(56) References Cited

U.S. PATENT DOCUMENTS

| | | | |
|---|---|---|---|
| 10,640,578 B2 | 5/2020 | Krause et al. | |
| 11,000,467 B2 | 5/2021 | Krause | |
| 2006/0008475 A1 | 1/2006 | Johannes et al. | |
| 2006/0084759 A1 | 4/2006 | Calabro et al. | |
| 2011/0069475 A1 | 3/2011 | Mish et al. | |
| 2012/0004194 A1 | 1/2012 | Lu et al. | |
| 2012/0148523 A1 | 6/2012 | Lu | |
| 2018/0318203 A1 | 11/2018 | Krause | |

FOREIGN PATENT DOCUMENTS

| | | | | |
|---|---|---|---|---|
| CN | 102770459 A | 11/2012 | | |
| CN | 105616184 | 8/2018 | | |
| JP | 2009529086 A | 8/2009 | | |
| JP | 2019509385 A | 4/2019 | | |
| WO | 1995015168 A1 | 6/1995 | | |
| WO | 00/016818 A1 | 3/2000 | | |
| WO | 2009/108100 A1 | 9/2009 | | |
| WO | WO-2011002956 A1 * | 1/2011 | ............. | C08B 15/02 |
| WO | 2011/069475 A2 | 6/2011 | | |
| WO | 2011/100469 A1 | 8/2011 | | |
| WO | 2016097211 A1 | 6/2016 | | |
| WO | 2017/063749 A1 | 4/2017 | | |
| WO | 2017162676 | 9/2017 | | |
| WO | WO-2017162676 A1 * | 9/2017 | ................ | C08L 5/08 |
| WO | 2021124147 A1 | 6/2021 | | |

OTHER PUBLICATIONS

PCT International Search Report for PCT/EP2019/085829, mailed Mar. 4, 2020.
Dahlmann, et al., "Fully defined in situ cross-linkable alginate and hyaluronic acid hydrogels for myocardial tissue engineering," Biomaterials, (2013), vol. 34, No. 4: 940-951.
D'Este, et al., "A systematic analysis of DMTMM vs EDC/NHS for ligation of amines to Hyaluronan in water," Carbohydrate Polymers, (2014), vol. 108: 239-246.
Moeller, et al., "Preparation and evaluation of hydrogel-composites from methacrylated hyaluronic acid, alginate, and gelatin for tissue engineering," Int. J. Artif. Organs, (2011), vol. 34, No. 2: 93-102.
Shu, et al., "Disulfide Cross-Linked Hyaluronan Hydrogels," Biomacromolecules, (2002), vol. 3: 1304-1311.
Tan, et al., "Injectable In Situ Forming Biodegradable Chitosan-Hyaluronic acid Based Hydrogels for Cartilage Tissue Engineering," Biomaterials, (2009), vol. 30, No. 13: 2499-2506.
Hoyle, et al., "Thiol-click chemistry: a multifaceted toolbox for small molecule and polymer synthesis," Chem. Soc. Rev., (2010), vol. 39: 1355-1387.
Van Dijk, et al., "Synthesis and Applications of Biomedical and Pharmaceutical Polymers via Click Chemistry Methodologies," Bioconjug. Chem., (2009), vol. 20, No. 11: 2001-2016.
Ossipov, et al., "Functionalization of Hyaluronic Acid with Chemoselective Groups via a Disulfide-Based Protection Strategy for In Situ Formation of Mechanically Stable Hydrogels," Biomacromolecules, (2010), vol. 11: 2247-2254.

(Continued)

*Primary Examiner* — Bethany P Barham
*Assistant Examiner* — Judith Marie Kamm
(74) *Attorney, Agent, or Firm* — McBee Moore & Vanik IP, LLC

(57) ABSTRACT

A modified hyaluronic acid derivative is described having the —CH2-OH group of the N-acetyl-D-glucosamine unit (GlcNAc) modified to an aldehyde group having the structure —CH2-O—CH2-CHO where the degree of modification is 1.0% to 15.0% for preparing a crosslinked hydrogel for use in aesthetic applications. The modified hyaluronic acid derivative is prepared by reacting a glycerol-modified hyaluronic acid with an oxidizing agent such as periodate.

17 Claims, 3 Drawing Sheets

(56) References Cited

OTHER PUBLICATIONS

Varghese, et al., "In Situ Cross-Linkable High Molecular Weight Hyaluronan-Bisphosphonate Conjugate for Localized Delivery and Cell-Specific Targeting: A Hydrogel Linked Prodrug Approach," J. Am. Chem. Soc., (2009), vol. 131: 8781-8783.
Oommen, et al., "Smart Design of Stable Extracellular Matrix Mimetic Hydrogel: Synthesis, Characterization, and In Vitro and In Vivo Evaluation for Tissue Engineering," Adv. Funct. Mater., (2013), vol. 23: 1273-1280.
Kablik, et al., "Comparative Physical Properties of Hyaluronic Acid Dermal Fillers," Dermatol. Surg, (2009), vol. 35: 302-312.
Yan Xiaoli et al.: "Preparation and characterization of collagen/oxidized hyaluronic acid composite hydrogel scaffolds", "China Practical Medicine." vol. 6, No. 29, pp. 3-5, Oct. 2011. English abstract included.
Hu Guoying et al.: "Preparation and medical application progress of cross-linked and esterified derivatives of hyaluronic acid", "Dialysis and Artificial Organs" vol. 14 No. 3, pp. 30-46, Sep. 2003. English abstract included.
Sigaeva et al., "Chemical modifications of hyaluronic acid and its application in medicine" Bulletin of Bashkir University (2012) 17(3). 1220-1241. Summary and machine English translation attached.
Hokputsa et al., "A comparison of molecular mass determination of hyaluronic acid using SEC/MALLS and sedimentation equilibrium," European Biophysics Journal, vol. 32, 2003, pp. 450-456. Abstract included.
Kinoshita et al., "Determination of molecular mass of acidic polysaccharides by capillary electrophoresis," Biomedical Chromatography, vol. 16, 2002, pp. 141-145. Abstract included.
Sundaram et al., "Cohesivity of Hyaluronic Acid Fillers Development and Clinical Implications of a Novel Assay, Pilot Validation with a Five-Point Grading Scale, and Evaluation of Six U.S. Food and Drug Administration-Approved Fillers," Plastic and Reconstructive Surgery, vol. 136, 2015, pp. 678-686. Summary included.
Kim et al., "Structural and antioxidant properties of gamma irradiated hyaluronic acid." Food Chemistry, 109(4), 763-770, https://doi.org/10.1016/j.foodchem.2008.01.038 (2008). Summary included.

* cited by examiner

ALDEHYDE-MODIFIED HYALURONIC ACID, METHOD FOR PREPARING SAME AND APPLICATIONS THEREOF

CROSS-REFERENCE TO RELATED APPLICATIONS

This application is the National Stage entry of International Application No. PCT/EP2019/085829, filed 18 Dec. 2019, which claims priority to European Patent Application No. 18214028.5, filed 19 Dec. 2018, and European Patent Application No. 19191042.1, filed 9 Aug. 2019.

BACKGROUND

Field

FIELD OF THE INVENTION

The present invention relates to a modified hyaluronic acid derivative, methods for preparing thereof and uses thereof. The novel modified hyaluronic acid derivative is characterized in that the —$CH_2$—OH group of at least one N-acetyl-D-glucosamine unit is modified into an aldehyde group having the structure —$CH_2$—O—$CH_2$—CHO.

Description of Related Art

Injectable fillers are today used in numerous therapeutic and aesthetic applications for adding volume to soft tissues. In aesthetic medicine, dermal fillers are increasingly used for the rejuvenation of the face and selected areas of the body. They allow enhancement of facial features (e.g., cheeks and lips), reduction of wrinkles (e.g., nasolabial folds) and creases, and can restore some of the lost volume and elasticity of the skin and underlying tissues that occurs with ageing. This makes the skin look smoother and fuller and, thus, provides a more youthful appearance.

A wide variety of materials are known for use in soft tissue fillers. Most of these materials have a temporary effect (about three to eighteen months) because they are resorbed in the body (e.g., collagen, hyaluronic acid (HA), poly-L-lactic acid (PLLA)). There are also a few permanent (i.e. non-absorbable) fillers, such as an FDA-approved filler material that is based on polymethylmethacrylate beads (PMMA microspheres). Several of these known soft tissue fillers contain lidocaine (a local anesthetic agent) which is added to decrease pain or discomfort related to the injection.

Today, the most commonly used material in soft tissue fillers worldwide is hyaluronic acid (HA). This is due to its excellent ability to create volume and favorable safety profile. HA is a naturally occurring glycosaminoglycan present in the extracellular matrix of, e.g., the dermis and is composed of alternating residues of β-D-(1→3) glucuronic acid (GlcUA) and β-D-(1→4)-N-acetylglucosamine (GlcNAc). HA is able to combine with water and swell when in gel form, causing a smoothing/filling effect. In most cases, HA used in dermal fillers is crosslinked to make it last longer in the body (up to eighteen months).

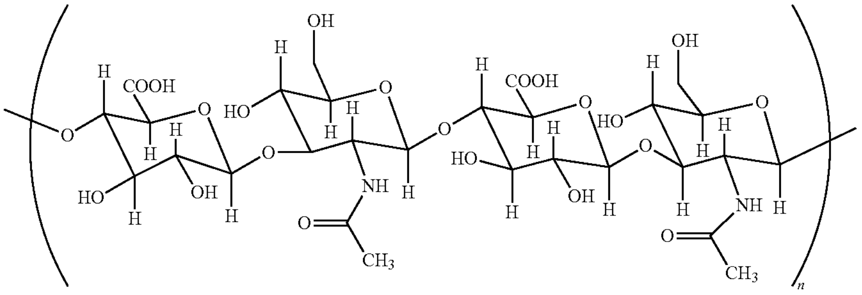

GlcUA GlcNAc GlcUA GlcNAc

Various crosslinking approaches for covalently binding the polymer chains of polysaccharides (e.g., HA) molecules together to form a filler material matrix with inter- and intramolecular cross-links are known in the art. A widely used approach is chemical crosslinking with chemical agents. These agents commonly react with the polysaccharide's hydroxyl and/or carboxyl functional groups. Commonly used cross-linking agents include, without limitation, DVS (divinylsulfone), di- or multi-functional epoxides (e.g., 1,4-butanediol diglycidyl ether (BDDE)), 1,2-bis(2,3-epoxypropoxy)ethylene (EGDGE) and 1,2,7,8-diepoxyoctane (DEO)), PEG-based crosslinking agents (e.g., pentaerythritol tetraglycidyl ether (PETGE)), biscarbodiimides (BCDI) (e.g., phenylenebis-(ethyl)-carbodiimide and 1,6-hexamethylenebis-(ethylcarbodiimide)), di-amine or multiamine cross-linkers (e.g., hexamethylenediamine (HMDA) and 3-[3-(3-aminopropoxy)-2,2-bis(3-amino-propoxymethyl)-propoxy]-propylamine (4 AA)), bis(sulfosuccinimidyl)suberate (BS), 1-(2,3-epoxypropyl)-2,3-epoxycyclohexane, epichlorohydrin, aldehydes (e.g., formaldehyde and glutaraldehyde), and hydrazides (bis-, tris- and polyvalent hydrazide compounds, e.g., adipic dihydrazide (ADH)).

Other methods that have been employed for cross-linking of injectable polysaccharide hydrogels include photochemical cross-linking of methacrylated polymers (Mller et al., Int. J. Artif. Organs 2011, 34:93-102), Michael addition cross-linking (Shu et al., Biomacromolecules 2002, 3:1304-1311), Schiff-base reaction cross-linking (Tan et al., Biomaterials 2009, 30:2499-2506), "click" chemistry approaches using reactions like the thiol-ene reaction or the azide-alkyne cycloaddition (Hoyle et al., Chem. Soc. Rev. 2010, 39:1355-1387; van Dijk et al., Bioconjug. Chem. 2009, 20:2001-2016). Polysaccharide-based photocrosslinked fillers for augmenting soft tissue are also known in the art (see, e.g., US 2011/069475). In addition, the esterification of carboxyl functions of acid polysaccharides with hydroxyl groups of the same or different polysaccharide molecule, thereby forming "inner" inter- and/or intramolecular ester-based cross-links (referred to as "autocross-linked polymer" or "ACP") has been investigated in the art. Furthermore, US 2006/0084759 describes a tyramine-modified and crosslinked HA hydrogel material, wherein cross-linking is achieved via peroxidase-mediated dityramine-linkages that can be performed in vivo.

The most commonly used approach for preparing cross-linked fillers is performing crosslinking by means of BDDE. However, BDDE and its degradation products are small molecular weight compounds which are toxicologically harmful and thus need to be thoroughly removed from the final product. The upper limit of the BDDE content in dermal fillers (for the most markets) is below 2 ppm. Thus, it has to be made sure that virtually all BDDE molecules (and their degradation products) are removed from the product. Hence, an important but also highly time-consuming part of the process for preparing a BDDE-crosslinked filler is its purification after crosslinking. A widely used purification technique is dialysis. However, even though dialysis is very effective in removing undesired toxic impurities (i.e. BDDE and its degradation products), it is very time consuming, i.e. it often takes up to several days. Therefore, the production of BDDE-crosslinked fillers consists of numerous, quite complex process steps which require long time, mostly several days, which significantly increases the cost of the final product. Also, since dialysis is mostly done manually, it is a potential source for gel contamination. Thus, methods for preparing crosslinked fillers that overcome the above drawbacks are highly sought after.

Also, conventional pre-formed hydrogels often suffer from the drawback that they are highly viscous, which impedes their injection through fine needles. One approach of addressing that issue is to use in situ gelling hydrogel compositions. These compositions are injected in the tissue in liquid form rather than in the form of a pre-formed gel, and crosslink at the site of injection to form an in situ crosslinked gel. Another approach for addressing that issue is to add a lubrication phase (e.g., uncrosslinked polysaccharide, e.g., HA) to the cross-linked hydrogel, which decreases injection force. However, when the hydrogel to be injected has a rather low viscosity, it has been shown that a lubrication phase is not necessarily needed.

A number of in situ formed gels use an aldehyde-modified polysaccharide (e.g., HA) derivative that is crosslinked in situ with another polysaccharide (e.g., HA) derivative to form a crosslinked gel. Also, using an aldehyde-modified polysaccharide (e.g., HA) derivative that forms a cross-linked gel upon reaction with another complementary polysaccharide (e.g., HA) derivative, overcomes the above issues with regard to BDDE crosslinking, because no BDDE is needed. Thus, aldehyde-modified polysaccharide (e.g., HA) derivatives are promising candidates for preparing BDDE-free crosslinked fillers.

In this respect, reference may be made to WO 00/016818 which discloses the in situ formation of a hydrogel by cross-linking an aldehyde- (or amine-) functionalized derivative of HA (e.g., adipic dihydrazido-HA) with a homo- or heterobifunctional cross-linker (e.g., a bifunctional N-hydroxysuccinimide ester cross-linker such as $(SPA)_1$-PEG). Further, WO 2011/100469 discloses a cross-linked HA hydrogel for use as a vitreous substitute biomaterial made by reacting oxidized HA bearing aldehyde functional groups (oxi-HA) with a dihydrazide cross-linker, e.g., adipic acid dihydrazide (ADH). WO 2009/108100 discloses a HA-based hydrogel prepared in situ by mixing aldehyde-modified HA and a hydrazide-modified polyvinyl-alcohol (PVAH) crosslinking reagent to form a cross-linking structure that exhibits a plurality of hydroxyl groups.

In addition, WO 2011/069475 discloses a method for preparing an aldehyde-HA derivative containing an aldehyde group by oxidation of the primary hydroxyl group at C6 of the glucosamine repeat unit using a TEMPO (2,2,6,6-tetramethyl-piperidinyloxyl)/co-oxidant system, and the use of said aldehyde-HA derivative for preparing cross-linked HA hydrogels by reacting with a diamine compound (e.g., hexanediamine) or amine-HA (e.g., hexanediamine substituted HA). Furthermore, WO 2017/063749 discloses the use of a first hyaluronic acid derivative and a second hyaluronic acid derivative, wherein the first hyaluronic acid derivative is functionalized with a hydrazide moiety and the second hyaluronic acid derivative is functionalized with an aldehyde moiety, for the in situ formation of a cross-linked hydrogel at the target site. The second aldehyde-functionalized hyaluronic acid derivative may be made by oxidation of a primary hydroxyl ($—CH_2OH$) group into an aldehyde (—CHO) group.

Moreover, the non-patent literature also discloses in situ formed gels using an aldehyde-modified polysaccharide derivative. For example, Dahlmann et al. (Biomaterials 2013, 34:940-951) describes fully defined in situ cross-linkable alginate and HA hydrogels for myocardial tissue engineering. The hydrogels are prepared by reacting aldehyde and hydrazide functionalized alginate and HA in the presence of human type I collagen and neonatal rat heart cells (NRHC) to yield a hydrazone cross-linked hydrogel-based bioartificial cardiac tissue. Further, Ossipov et al. (Biomacromolecules 2010, 11:2247-2254) discloses the synthesis of hydrazide functionalized HA using a specific symmetrical di-functional reagent having a central divalent protecting group that can undergo an amide-type reaction with the carboxylate residue of HA in aqueous solution. The hydrazide functionalized HA can be used for the in situ formation of a hydrazone HA hydrogel by mixing with an aldehyde HA derivative.

Varghese et al. (J. Am. Chem. Soc. 2009, 131:8781-8783) reports on a HA derivative that is dually-functionalized with a hydrazide group and an aminomethylene bisphosphonate group capable of covalently binding bisphosphonate (BP; an antiosteoclastic and antineoplastic small molecule drug). Mixing of said dually functionalized HA with aldehyde functionalized HA results in the in situ formation of an injectable HA hydrogel for the controlled release of the BP drug at the site of implantation. Oommen et al. (Adv. Funct. Mater 2013, 323:1273-1280) describes a HA hydrogel prepared by mixing a HA-aldehyde derivative with a carbodihydrazide (CDH) functionalized HA derivative to obtain a HA hydrogel with hydrazone bonds. It is further described that the in situ HA hydrogel formation in the presence of a therapeutic protein (e.g., the recombinant human growth factor BMP-2) afforded a hydrogel for in vivo applications that is capable of delivering growth factors for bone tissue regeneration.

However, the usually applied methods for adding aldehyde functional groups to hyaluronic acid show a number of drawbacks. For example, introducing aldehyde groups by means of periodate oxidation of unfunctionalized hyaluronic acid usually leads to a breakage of the cyclic saccharide rings of the polysaccharide backbone, which decreases the overall stability of the hyaluronic acid and adds undesired flexibility to the polysaccharide backbone. Specifically, frequently used reactions for introducing aldehyde functional groups to hyaluronic acid, e.g., oxidation with sodium periodate, require long reaction times and/or are difficult to control with regard to an undesired oxidation to carboxylic acid groups.

Furthermore, there exists no universal filler that is appropriate for every application or for every patient. For example, gels of different stiffness/hardness (often expressed by means of the elastic modulus) are required for different applications. In view of the relatively high dynamic forces occurring during facial muscle movement, gels with a higher stiffness are usually desired for correction in areas such as nasolabial folds and marionette lines. In contrast, gels with lower stiffness are better suited for areas where resistance to deformation is not crucial or where anatomy does not require stiffness but volume and softness are important, e.g. in lips (see e.g. Kablik et al., Dermatol Surg, 2009, 35, 302-312).

However, the properties, e.g. the stiffness, of a hydrogel prepared from an aldehyde-modified polysaccharide (e.g., HA) derivative and a complementary polysaccharide (e.g., HA) derivative (crosslinked in situ, i.e. after injection of the two complementary polysaccharide derivatives; or crosslinked in vitro, i.e. prior to injection) depend, to a large degree, on the properties of the specific modified polysaccharide (e.g. modified hyaluronic acid), in particular its molecular weight and degree of modification. For instance, an aldehyde-modified hyaluronic acid having a very low degree of aldehyde modification (i.e. very low number of aldehyde groups) will have a relatively low amount of crosslinks formed and, thus, the resulting gel will be rather soft. Therefore, different aldehyde-modified hyaluronic acids are used for different applications. While an aldehyde-modified hyaluronic acid leading to "softer" hydrogels (e.g. an aldehyde-modified hyaluronic acid having a low degree of modification) may be used for lip fillers, an aldehyde-modified hyaluronic acid leading to "harder" hydrogels (e.g., an aldehyde-modified hyaluronic acid having a high degree of modification) may be used for fillers for nasolabial folds or marionette lines.

Thus, methods for producing modified hyaluronic acid for the in vitro or in situ formation of crosslinked gels, e.g., aldehyde-modified hyaluronic acid, which allow for modifying (fine-tuning) the properties of the resulting aldehyde-modified hyaluronic acid are generally highly sought after. In particular, methods are desired that allow for an easy modification of the properties of a resulting aldehyde-modified hyaluronic acid without significantly modifying the overall synthesis method, i.e. keeping most parameters constant while only changing easy-modifiable parameters, e.g. starting material concentration, amount of oxidizing agent and reaction time. With such a method the same or similar experimental setup could be used for producing different aldehyde-modified hyaluronic acids exhibiting different properties (e.g., different degree of modification and molecular weight).

OBJECT OF THE INVENTION

In view of the above, it is an object of the present invention to provide a versatile and convenient method for producing an aldehyde-modified hyaluronic acid suitable for the in vitro or in situ formation of a crosslinked hyaluronic acid-based hydrogel. Furthermore, it is an object of the present invention to provide such an aldehyde-modified hyaluronic acid that is particularly suitable for aesthetic applications. It is also an object of the present invention to provide a hydrogel prepared from an aldehyde-modified hyaluronic acid that is particularly suitable for aesthetic applications.

SUMMARY OF THE INVENTION

The above object is solved by the provision of a novel modified hyaluronic acid derivative (also referred to herein as "aldehyde-modified hyaluronic acid derivative" or "aldehyde-modified hyaluronic acid") and a method for preparing the same. The new modified hyaluronic acid derivative has the $-CH_2-OH$ group of at least one N-acetyl-D-glucosamine unit modified into an aldehyde group having the structure $-CH_2-O-CH_2-CHO$ and is useful for the in vitro and in situ formation of a crosslinked hydrogel when it is reacted with a second polysaccharide derivative, which comprises one or more nucleophilic functional groups capable of forming a covalent bond with one or more aldehyde groups of the new modified hyaluronic acid derivative.

The two functionalized polysaccharide derivatives (i.e. the new modified hyaluronic acid derivative and the second polysaccharide derivative) can be co-injected in liquid form, thereby enabling co-injection with low extrusion forces even through fine needles. Desirably, the in situ gel formation does not generate any harmful by-products. The only by-product is water that is readily absorbed by the formed hydrogel and/or the surrounding tissues. In addition, the in situ formed hydrogel has the desired properties in terms of tissue integration, skin improvement, tissue shaping capacity and volumizing ability.

Also, it has surprisingly been found that the new aldehyde-modified hyaluronic acid derivative is suitable for the in vitro preparation of crosslinked gels via reaction with a second, complementary, polysaccharide derivative, preferably also a hyaluronic acid derivative. In particular, it has been found that the properties of a such prepared gel cannot only be controlled by means of the properties of the single derivatives (e.g. the degree of modification and molecular weight) but also by tuning the concentrations of the respective polysaccharide derivatives in the medium used for crosslinking.

Advantageously, the aldehyde group having the structure $-CH_2-O-CH_2-CHO$ is just long enough to provide a good steric availability for crosslinking but is short enough to not add too much flexibility to the crosslinked gel. This makes the new modified hyaluronic acid derivative particularly suitable for the in situ formation of gels covering a wide range of stiffnesses. For example, using a new modified hyaluronic acid derivative with a high degree of modification (i.e. a large number of aldehyde groups) leads to the formation of a high number (due to the high number of sterically well available aldehyde groups) of comparatively short crosslinks, thereby leading to the formation of a relatively hard gel.

The modified hyaluronic acid derivative of the present invention can be prepared from a glycerol-modified hyaluronic acid, which is characterized in that the $-CH_2-OH$ group of at least one N-acetyl-D-glucosamine unit is modified into a moiety of the following formula $-CH_2-O-CH_2-CHOH-CH_2OH$ by means of oxidizing said $-CH_2-O-CH_2-CHOH-CH_2OH$ group into an aldehyde group having the structure $-CH_2-O-CH_2-CHO$. This novel method of preparing the new modified hyaluronic acid derivative avoids the drawbacks of the usually used methods for preparing aldehyde-modified hyaluronic acid derivatives, such as long reaction times, dramatic decrease of the molecular weight of the hyaluronic acid, or an undesired oxidation to a carboxylic acid group.

It has been shown that by using this method, the properties of the new modified hyaluronic acid derivative can easily be tuned by only changing basic parameters such as the starting material concentration, amount of oxidizing agent and reaction time. For example, by varying the starting material concentration, amount of oxidizing agent and/or reaction time, it is possible to fine-tune the degree of modification and/or the molecular weight of the resulting new modified hyaluronic acid derivative.

In a first aspect, the present invention relates to a modified hyaluronic acid derivative, wherein the —$CH_2$—OH group of at least one N-acetyl-D-glucosamine unit is modified into an aldehyde group having the structure —$CH_2$—O—$CH_2$—CHO. Preferably, the modified hyaluronic acid derivative comprises at least one disaccharide unit of the following structure

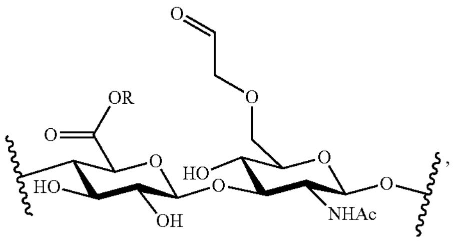

wherein Ac denotes —C(O)$CH_3$ and R is selected from hydrogen, an alkali metal ion, preferably Na, or an alkaline earth metal ion.

In a second aspect, the present invention relates to a method for preparing the modified HA derivative of the present invention. The method comprises the following steps: a) providing a glycerol-modified hyaluronic acid, which is characterized in that the —$CH_2$—OH group of at least one N-acetyl-D-glucosamine unit is modified into a moiety of the following formula —$CH_2$—O—$CH_2$—CHOH—$CH_2$OH; b) dissolving the glycerol-modified hyaluronic acid in an aqueous medium to obtain solubilized glycerol-modified hyaluronic acid; c) reacting said solubilized glycerol-modified hyaluronic acid with an oxidizing agent, preferably a periodate, more preferably sodium periodate, to convert at least a part of said —$CH_2$—O—$CH_2$—CHOH—$CH_2$OH groups into aldehyde groups having the formula —$CH_2$—O—$CH_2$—CHO, thereby obtaining an aldehyde-modified hyaluronic acid derivative.

In a third aspect, the present invention relates to a modified hyaluronic acid derivative obtained by the method of the present invention.

In a fourth aspect, the present invention relates to the use of the modified hyaluronic acid derivative of the present invention or a modified hyaluronic acid derivative obtained by the method of the present invention for the in situ formation of a crosslinked hydrogel in aesthetic applications.

In a fifth aspect, the present invention relates to the use of a modified hyaluronic acid derivative of the present invention or a modified hyaluronic acid derivative obtained by the method of the present invention for the formation of a pre-formed crosslinked hydrogel.

In a sixth aspect, the present invention relates to a modified hyaluronic acid derivative of the present invention or a modified hyaluronic acid derivative obtained by the method of the present invention for use in the in situ formation of a crosslinked hydrogel for therapeutic application.

The modified hyaluronic acid derivative is generally used together with a second polysaccharide derivative, which comprises one or more nucleophilic functional groups capable of forming a covalent bond with one or more aldehyde groups of the modified hyaluronic acid derivative, wherein the second polysaccharide is preferably a hyaluronic acid derivative and said nucleophilic functional group is preferably a hydrazide functional group, and wherein the second polysaccharide is more preferably a hyaluronic acid derivative comprising at least one disaccharide unit having the following structure:

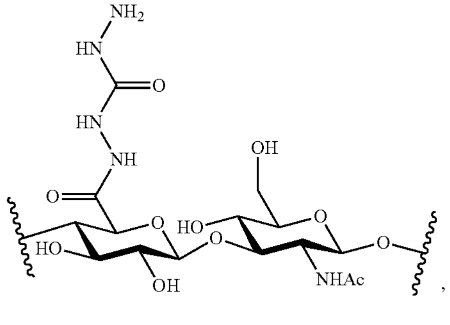

wherein "Ac" is as defined above.

In a seventh aspect, the present invention relates to a crosslinked hydrogel, comprising the following structural unit:

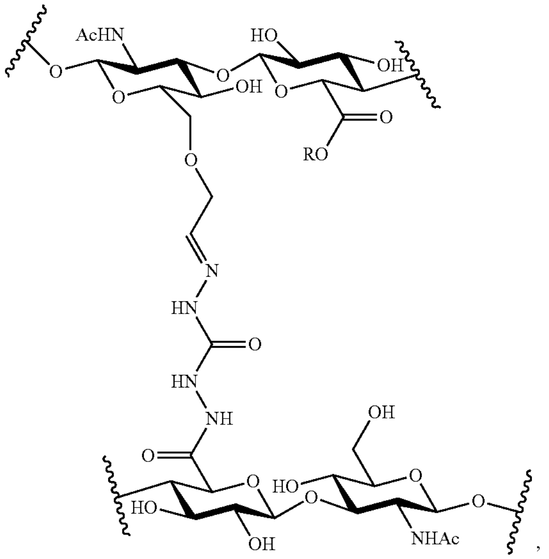

wherein "Ac" and R are as defined above.

In an eighth aspect, the present invention relates to a crosslinked hydrogel obtained by contacting the aldehyde-modified HA derivative of the present invention or a modified hyaluronic acid derivative obtained by the method of the present invention and a second polysaccharide derivative, which comprises one or more nucleophilic functional groups capable of forming a covalent bond with one or more aldehyde groups of the modified HA derivative, as defined herein.

In a ninth aspect, the present invention relates to a method, preferably an aesthetic method, of preparing a crosslinked hydrogel, the method comprising the following steps: a) providing a first precursor solution comprising the modified hyaluronic acid derivative of the present invention or a modified hyaluronic acid derivative obtained by the method of the present invention and, separately thereof, a second precursor solution comprising the second polysaccharide derivative as defined herein; b) mixing the first precursor solution and the second precursor solution into an in situ crosslinkable mixture; and c) injecting the in situ crosslinkable mixture to a target site in the body of a patient to form a crosslinked gel at the target site.

In a tenth aspect, the present invention relates to a method for preparing a crosslinked hydrogel, preferably a pre-formed crosslinked hydrogel.

In an eleventh aspect, the present invention relates to a kit for the in situ formation of a crosslinked hydrogel, comprising (i) a first container containing a first precursor solution comprising the modified hyaluronic acid derivative of the present invention or a modified hyaluronic acid derivative obtained by the method of the present invention and (ii) a second container containing a second precursor solution comprising the second polysaccharide derivative as defined herein, and optionally, (iii) instructions for use.

Particular embodiments of the present invention are set forth in the appended claims.

BRIEF DESCRIPTION OF THE DRAWINGS

For a more complete understanding of the present invention, reference is made to the following description and accompanying drawings, in which.

DETAILED DESCRIPTION OF A PREFERRED EMBODIMENT

Figure 1:
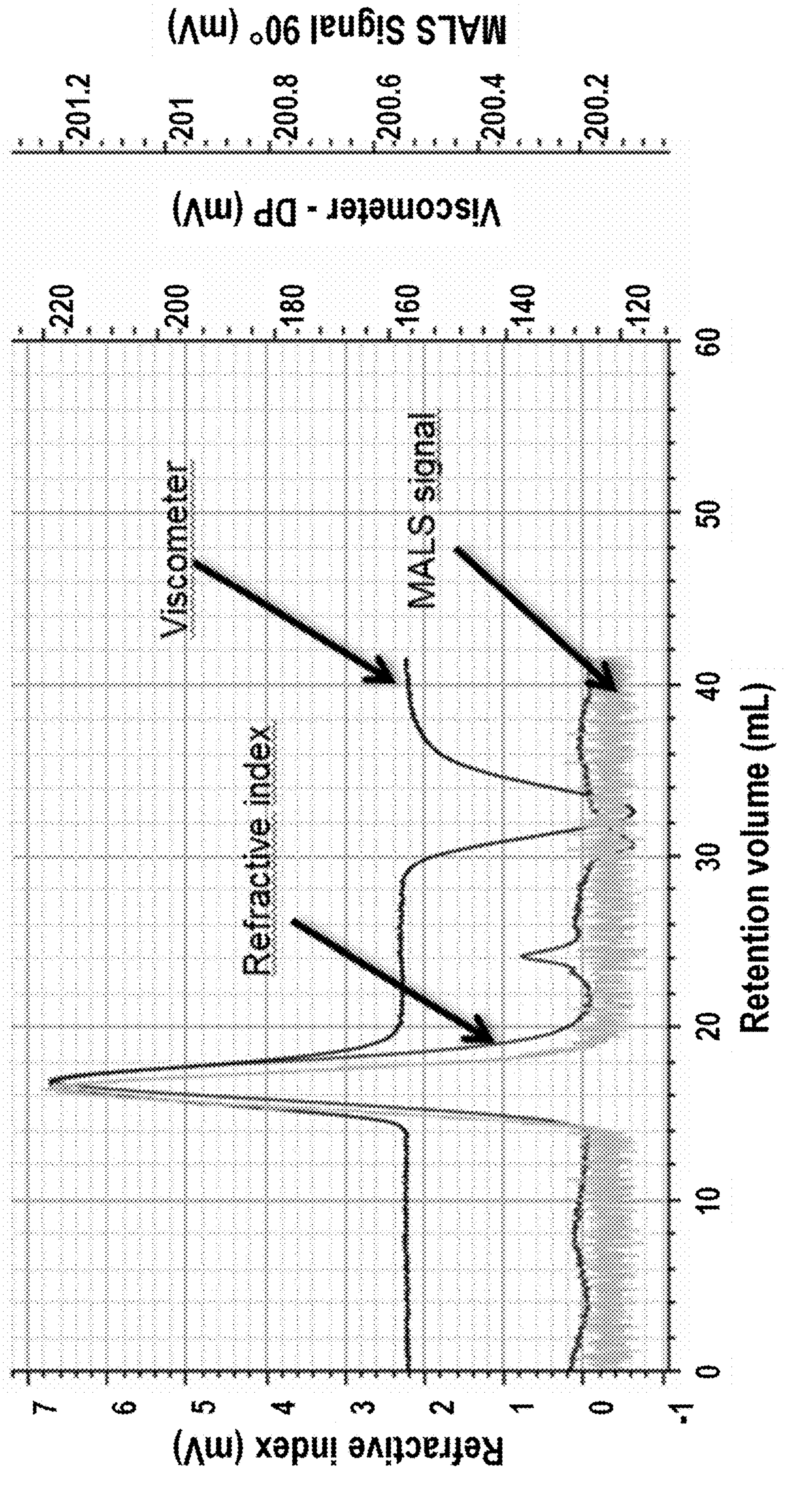
FIG. 1 shows an exemplary chromatogram obtained for determining the molecular weight.

The present invention is based on the surprising finding that the aldehyde-modified hyaluronic acid can be easily prepared from glycerol-modified hyaluronic acid. In particular, it has been found that the preparation of aldehyde-modified hyaluronic acid from glycerol-modified hyaluronic acid does not show the drawbacks that typically occur in the preparation of aldehyde-modified hyaluronic acid, such as a dramatic decrease in molecular weight, long reaction times, and undesired side-reactions (e.g., oxidation to carboxylic acid). Even more, it has been found that the properties of the resulting aldehyde-modified hyaluronic acid derivative can easily be modified (fine-tuned) by only modifying basic parameters such as the starting material concentration, amount of oxidizing agent and reaction time.

In particular, it has been found that the degree of modification and the molecular weight of the resulting aldehyde-modified hyaluronic acid derivative can be fine-tuned by varying the starting material concentration (i.e. the concentration of glycerol-modified hyaluronic acid), the amount of the oxidizing agent and the reaction time. This is particularly advantageous, because the degree of modification and molecular weight of the resulting aldehyde-modified hyaluronic acid derivative directly influence the gelation performance of said aldehyde-modified hyaluronic acid derivative. Thus, aldehyde-modified hyaluronic acid derivatives having different properties and thus leading to cross-linked gels with different properties, e.g., hardness, can be prepared by means of only one general synthetic method.

Furthermore, it has been found that the modified hyaluronic acid derivative of the present invention is particularly suitable for both the in situ and in vitro formation of a crosslinked hydrogel, i.e. it shows good crosslinking properties. In particular, it has been found that the modified hyaluronic acid derivative of the present invention shows good crosslinking properties with a second polysaccharide derivative, which comprises one or more nucleophilic functional groups capable of forming a covalent bond with one or more aldehyde groups of the modified hyaluronic acid derivative. In this regard, it has been found that the modified hyaluronic acid derivative of the present invention and said second polysaccharide derivative rapidly and efficiently crosslink to form a covalently crosslinked hydrogel, for example at a target site in the body. No additives, no catalysts, no pH switch, no UV irradiation nor any other external stimuli (or "triggers") are required to induce the crosslinking reaction. In particular, no crosslinker is used or required. The only by-product generated by the cross-linking reaction is typically water that is readily absorbed by the hydrogel and/or the surrounding tissues if crosslinking occurs in situ.

As used herein, the term "glycerol-modified hyaluronic acid" refers to hyaluronic acid, which is characterized in that the $—CH_2—OH$ group of at least one N-acetyl-D-glucosamine units is modified into a moiety of the following formula $—CH_2—O—CH_2—CHOH—CH_2OH$. Glycerol-modified hyaluronic acid is commercially available from "htl biotech", France, or may be prepared by grafting glycidol to hyaluronic acid in accordance with the following reaction scheme:

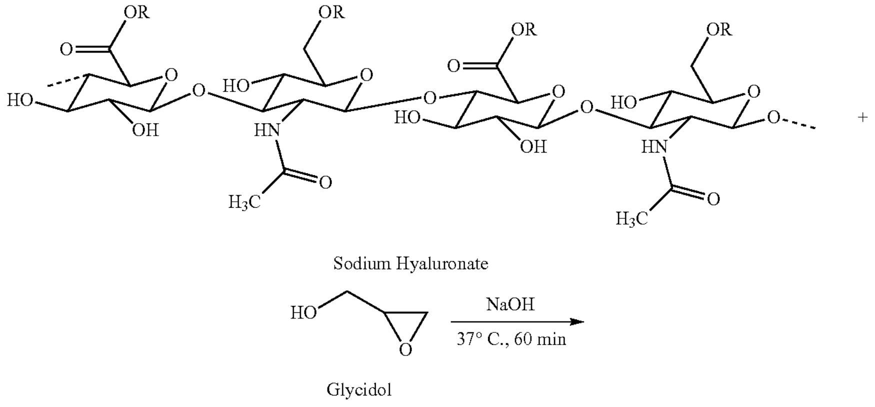

-continued

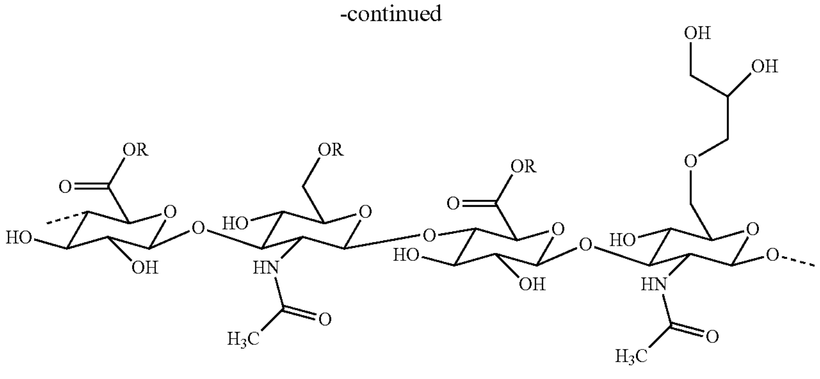

glycerol-modified Sodium Hyaluronate

Preferably, besides the —OH group bound to the C6 carbon of the GlcNac unit, no other groups are modified by means of the reaction with glycidol. Preferably, the glycerol-modified hyaluronic acid contains 1 to 100, preferably 2 to 50, more preferably 5 to 20, and most preferably 10 to 20 $—CH_2—O—CH_2—CHOH—CH_2OH$ groups per 100 N-acetyl-D-glucosamine units present in the hyaluronic acid. It has been shown that that degree of modification is particularly suited to subsequently prepare the aldehyde modified hyaluronic acid derivative of the present invention having the desired degree of (aldehyde) modification for preparing a crosslinked hydrogel for aesthetic applications by means of a reaction with a complementary second polysaccharide derivative, preferably a hyaluronic acid derivative. It is pointed out that within the meaning of the present invention, other functional groups of hyaluronic acid, i.e. other —OH groups and —COOH groups, in particular other (secondary) —OH groups, may be glycerol-modified, albeit in a much lesser extent. However, within the present invention, the glycerol-containing moiety is preferably only, essentially only or predominantly present at the C6 carbon of the GlcNac unit.

As used herein, the term “in situ” means at the site of administration, i.e. inside a patient’s body. Thus, in order to form a hydrogel “in situ”, i.e. at the site of administration, the modified hyaluronic acid derivative of the present invention is generally co-injected with a second polysaccharide derivative, which comprises one or more nucleophilic functional groups capable of forming a covalent bond with one or more aldehyde groups of the modified hyaluronic acid derivative of the present invention, or these compounds are otherwise applied together to a specific site (target site) within a patient’s body, e.g., a site in need of tissue augmentation for aesthetic reasons, and allowed to covalently crosslink at the site of co-injection. Within the present invention, the terms “in situ” and “in vivo” may be used interchangeably. A “patient” in the sense of the present invention may be any individual or subject, e.g., a mammal and, preferably, a human, in need of a “treatment” of a particular condition, state or disease, e.g., for cosmetic, aesthetic or therapeutic purposes. Thus, it is to be understood that the term “treatment”, as used herein, does not only refer to therapeutic/medical treatments but also includes, e.g., cosmetic and aesthetic treatments.

As used herein, the term “in vitro” means outside a human or animal body. Likewise, the term “pre-formed hydrogel”, “pre-formed gel”, or the like, as used herein, refers to a hydrogel that is formed outside a human or animal body. Thus, it is to be understood that the terms “pre-formed” and “in vitro” both describe that the hydrogel is formed outside a human or animal body prior to injection. Thus, a gel that has been prepared “in vitro” is a “pre-formed” gel, i.e. a gel that is formed outside a human or animal body.

As used herein, the term “artificial container” refers to any container that is not a human or animal body, or a part thereof. Preferably, the artificial container is made from a non-biological material, preferably glass or a plastic material, more preferably glass.

Within the context of the present invention, the term “co-injection” generally means that the modified hyaluronic acid derivative of the present invention and said second polysaccharide derivative are injected together as a single liquid composition, e.g., solution, to a target site in the body of a patient. The term “injectable” or “injection”, as used herein, indicates that the in situ hydrogel forming composition can be dispensed from a syringe or a syringe system. In particular, the term “co-injection” preferably means that the modified hyaluronic acid derivative of the present invention and said second polysaccharide derivative are mixed, in particular homogenously mixed, prior to exiting from the tip of the needle and entering the target site in the body of a patient, and then injected as a mixture to a target site in the body of a patient. Within the present invention, the terms “injection” or “co-injection” may refer to intra-, inter- or subdermal injection or subcutaneous injection. Further, the term “needle”, as used herein, is intended to comprise or be synonymous to a “cannula” or any other needle-like objects suitable for injection.

The terms “hydrogel” or “gel”, as used herein, mean a water-swollen three-dimensional network consisting of covalently cross-linked polymer chains. Preferably, the cross-linked (or “gelled”) hydrogel is cohesive. The term “cohesive” or “cohesivity” within the meaning of the present invention is defined as the capacity of a material (e.g., of a hydrogel) not to dissociate, because of the affinity of its molecules for each other. Cohesivity is a key characteristics of gel implants (e.g., the in situ gelled hydrogels described herein) and considered necessary for the solid and fluid phases of a gel to remain intact, and thus for gel integrity. In the context of the present invention, cohesivity of a polysaccharide hydrogel, in particular of a HA-based hydrogel, can be determined using the Gavard-Sundaram Cohesivity Scale (Sundaram et al., Plast. Reconstr. Surg. 136:678-686, 2015).

The term “spontaneous” or “spontaneously”, as used herein, is intended to refer to the fact that the aldehyde group of the modified hyaluronic acid derivative of the present invention and the nucleophilic group of the second polysaccharide derivative form a covalent linkage without any external stimuli (also referred to as "triggers") like heat or UV light. In particular, it has been found that the hydrogel can be formed spontaneously under in vivo conditions, i.e. after co-injection to a target site in the body of a patient, without any external stimuli (also referred to as "triggers") like heat or UV light, resulting in the in situ formation of a cross-linked polysaccharide hydrogel at the target site.

Within the present invention, an in situ (or in vivo) formed hydrogel is generally suitable for, is used as, and/or functions as a soft tissue filler. The term "soft tissue filler", as used herein, generally refers to a material designed to fill cavities and/or add volume to areas of soft tissue deficiency. This includes, e.g. augmenting, filling or replacing soft tissues. Herein, the term "soft tissue" generally relates to tissues that connect, support, or surround other structures and organs of the body. Soft tissues include, for example, muscles, tendons (bands of fiber that connect muscles to bones), fibrous tissues, fat, blood vessels, nerves, and synovial tissues (tissues around joints). In the context of the present invention, the soft tissue filler is preferably a dermal filler.

In a first aspect, the present invention relates to a modified hyaluronic acid derivative, wherein the $—CH_2—OH$ group of at least one N-acetyl-D-glucosamine unit is modified into an aldehyde group having the structure $—CH_2—O—CH_2—CHO$.

As set out above, it has been found that this modified hyaluronic acid derivative shows good crosslinking properties. Without wishing to be bound to any particular theory, it is believed that the good crosslinking properties are due to the steric properties of the aldehyde group introduced by means of the method of the present invention, i.e. the $—CH_2—OH$ group of at least one GlcNAc unit modified into an aldehyde group having the structure $—CH_2—O—CH_2—CHO$. Specifically, it is believed that said aldehyde group is just long enough to provide a good steric availability for crosslinking but is short enough to not add too much flexibility to the crosslinked gel.

Preferably the modified hyaluronic acid derivative contains no other chemical modification than an aldehyde group, preferably an aldehyde group present at the C6 carbon atom of the GlcNAc unit and having the structure $—CH_2—O—CH_2—CHO$.

Preferably, the modified hyaluronic acid derivative of the present invention has a degree of modification of 1.0% to 20.0%, more preferably 1.0% to 15.0%, even more preferably 1.0% to 10.0%, even more preferably 1.5% to 10.0%, even more preferably 1.5% to 8.0%, even more preferably 1.8% to 7.0%, even more preferably 2.0% to 6.9%. The degree of modification (MoD) is defined as the number of $—CH_2—O—CH_2—CHO$ groups divided by the total number of N-acetyl-D-glucosamine units present in the modified hyaluronic acid derivative. For example, a MoD of 15.0% means that the modified hyaluronic acid derivative contains 15 $—CH_2—O—CH_2—CHO$ groups per 100 N-acetyl-D-glucosamine units. A MoD of 37.0% means that the modified hyaluronic acid derivative contains 37 $—CH_2—O—CH_2—CHO$ groups per 100 N-acetyl-D-glucosamine units, and so on. It has been found that this rather low degree of modification is particularly suitable for preparing hydrogels for aesthetic applications where comparatively low viscosity hydrogels are required. Also, such low viscosity hydrogels can still be injected through fine needles, which allows for an in vitro preparation of a hydrogel (i.e. the formation of a pre-formed hydrogel), the properties of which can be thoroughly determined and checked, before injection, which, however, is not possible if the hydrogel is prepared in situ.

Since the hardness (or stiffness; e.g., as indicated by the elastic modulus) of a hydrogel formed from the modified hyaluronic acid derivative of the present invention depends on the number and density of crosslinks formed in said hydrogel and the number and density of crosslinks formed in said hydrogel directly depends on the degree of modification of the modified hyaluronic acid derivative of the present invention, the degree of modification directly affects the hardness of a hydrogel formed from the modified hyaluronic acid derivative of the present invention. Thus, the degree of modification is an important characteristic of the modified hyaluronic acid derivative of the present invention.

The degree of modification (MoD) may be determined via spectrometry and/or spectroscopy analytical methods, such as $^1H$ NMR, UV/Vis and IR, titration, HPLC, SEC, viscosity, among others. Conveniently, the degree of modification is determined by means of $^1H$ NMR. An exemplary method for determining the MoD is given in the Example Section.

The molecular weight (also referred to as molar mass) is another important characteristic of the modified hyaluronic acid derivative directly influencing the properties of a gel formed therefrom. Preferably, the modified hyaluronic acid derivative has a weight average molecular weight of 0.1 to 2.5 MDa, more preferably 0.2 to 1.5 MDa, even more preferably 0.4 to 1.3 MDa, even more preferably 0.6 to 1.1 MDa.

All numbers herein expressing "molecular weight", "molar mass", "mean molecular weight", "mean molar mass", "average molecular weight", and "average molar mass" of polysaccharides (e.g. HA) are to be understood as indicating the weight-average molecular weight (or mass-average molecular weight or weight-average molar weight) or $M_w$ (w is for weight) in Daltons (Da). The mass-average molar mass ($M_w$) is defined as follows: $M_w=\Sigma_i N_i M_i^2/\Sigma_i N_i M_i$, wherein Ni is the number of molecules of molar mass Mi.

Various methods can be applied herein to determine the molecular weight of HA, such as intrinsic viscosity measurements (e.g., European Pharmacopoeia 7.0—Hyaluronic Acid monograph No. 1472, January 2011), capillary electrophoresis (CE) (e.g., according to Kinoshita et al., Biomed. Chromatogr., 2002, 16:141-45), gel permeation chromatography (GPC) (e.g., according to Kim et al., Food Chem., 2008, 109:63-770), and multi-angle laser light scattering combined with size-exclusion chromatography (SEC-MALLS) (e.g., in accordance to Hokputsa et al., Eur. Biophys. J. Biophys. Lett., 2003, 32:450-456).

Within the framework of the present invention, the weight-average molecular weight ($M_w$) of HA polymers is preferably determined by gel permeation chromatography (GPC) or viscometry via the Mark-Houwink equation. The GPC technique involves eluting a polymer solution through a matrix of packed polymer particles at a pressure of up to several Megapascals (MPa). As well known to a skilled person, the use of low dispersity standards allows one to correlate retention time with molar mass.

In the context of the present invention, the mass-average molar mass ($M_w$) may also be determined by means of the Mark-Houwink equation, notwithstanding the fact that this is commonly referred to as the viscosity average molar mass or $M_v$. The Mark-Houwink equation gives a relation between intrinsic viscosity (η) and molecular weight M and allows determination of the molecular weight of a polymer from data on the intrinsic viscosity and vice versa. Within the context of the present invention, the intrinsic viscosity is preferably measured according to the procedure defined in European Pharmacopoeia 7.0 (Hyaluronic Acid monograph No. 1472, January 2011). Within the framework of the present invention, the average molecular weight is preferably the viscosity average molecular weight ($M_\eta$) which can be calculated from the intrinsic viscosity using the Mark-Houwink equation:

$$[\eta] = K \times M_\eta^a,$$

with [η]=intrinsic viscosity in $m^3$/kg, $M_\eta$=viscosity average molecular weight, K=$2.26\times10^{-5}$, and a=0.796, wherein, as set out above, the intrinsic viscosity is preferably measured according to the procedure defined in European Pharmacopoeia 7.0 (Hyaluronic Acid monograph No. 1472, January 2011).

The determination of the molecular weight is also exemplified the Example Section.

Preferably, the modified hyaluronic acid derivative comprises at least one disaccharide unit of the following structure

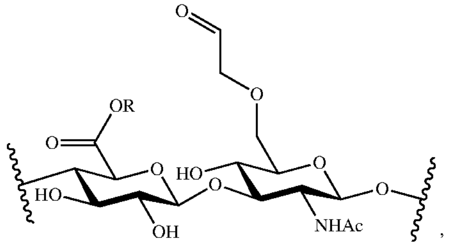

, wherein "Ac" denotes —C(O)$CH_3$ and R is selected from hydrogen, an alkali metal ion, preferably Na, or an alkaline earth metal ion. It is to be understood that instead of being present in protonated form (i.e. R=H), the carboxylic acid group can also be present deprotonated form (i.e. R=a negative charge) without any specific counterion being present to balance the negative charge. This situation occurs, e.g., in solution where the counter ion balancing the negative charge is solvated and located in random vicinity to the deprotonated carboxylic acid.

The modified hyaluronic acid derivative may further comprise at least one disaccharide unit of the following structure

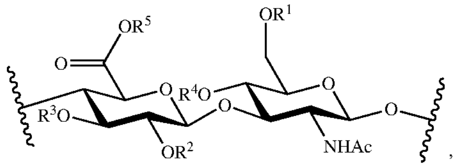

, wherein "Ac" is as defined above and $R^1$, $R^2$, $R^3$ and $R^4$ are independently selected from H and —$CH_2$—CHO and $R^5$ is selected from hydrogen, an alkali metal ion, preferably Na, an alkaline earth metal ion, and —$CH_2$—CHO, provided that at least one of $R^1$, $R^2$, $R^3$, $R^4$ and $R^5$ is —$CH_2$—CHO and, if $R^1$ is —$CH_2$—CHO, at least one of $R^2$, $R^3$, $R^4$ and $R^5$ is —$CH_2$—CHO.

Preferably, the number of aldehyde groups present at the C6 carbon atom of the GlcNAc unit (i.e., $R^1$=—$CH_2$—CHO) divided by the total number of aldehyde groups present in the modified hyaluronic acid derivative (including the aldehyde groups present at the C6 carbon atom of the GlcNAc unit) is 0.60 to 1, preferably 0.65 to 1, more preferably 0.70 to 1, even more preferably 0.75 to 1, even more preferably 0.80 to 1, even more preferably 0.85 to 1, even more preferably 0.90 to 1, even more preferably 0.95 to 1, even more preferably 0.97 to 1, even more preferably 0.98 to 1, even more preferably 0.99 to 1, most preferably 1.

In a second aspect, the present invention relates to a method for preparing the modified hyaluronic acid derivative of the present invention. The method comprises the following steps: a) providing a glycerol-modified hyaluronic acid, which is characterized in that the —$CH_2$—OH group of at least one N-acetyl-D-glucosamine unit is modified into a moiety of the following formula —$CH_2$—O—$CH_2$—CHOH—$CH_2$OH; b) dissolving the glycerol-modified hyaluronic acid in an aqueous medium to obtain solubilized glycerol-modified hyaluronic acid; c) reacting said solubilized glycerol-modified hyaluronic acid with an oxidizing agent to convert at least a part of said —$CH_2$—O—$CH_2$—CHOH—$CH_2$OH groups into aldehyde groups having the formula —$CH_2$—O—$CH_2$—CHO, thereby obtaining an aldehyde-modified hyaluronic acid derivative.

Preferably, the oxidizing agent is a periodate or lead(IV) acetate, preferably a periodate. More preferably, the oxidizing agent is sodium periodate.

As set out above, it has been found that the method of the present invention does not show the drawbacks that typically occur in the preparation of aldehyde-modified hyaluronic acid, such as a dramatic decrease in molecular weight, long reaction times, and undesired side-reactions (e.g., oxidation to carboxylic acid). For example, it has been found that even if sodium periodate is used as oxidant, which is known to oxidize the polymer backbone thereby leading to a breakage of the polymer backbone and to a reduction of the molecular weight of the hyaluronic acid, no or very little oxidation of the polymer backbone occurs in the method of the present invention.

The reason for this surprising behavior is the following: Periodate favors cis-diols over trans-diols; for oxidizing trans-diols with periodate, relatively harsh conditions and/or long reaction times are required. While the hydroxyl groups of the polymer backbone are oriented trans to each other, the —OH groups of the glycerol moiety (e.g. —$CH_2$—O—$CH_2$—CHOH—$CH_2$OH) are freely rotatable. Thus, the vicinal diol of the glycerol moiety is well accessible for periodate oxidation and the oxidation reaction (i.e. step c)) can be performed under mild conditions in a relatively short time such that no oxidation occurs at the polymer backbone. For example, it has been found that the oxidizing reaction of step c) can be carried out in less than one hour, even in 10 minutes.

Furthermore, it has been found that the properties of the resulting modified hyaluronic acid derivative of the first aspect can easily be modified (fine-tuned) by only modifying basic parameters, e.g. the starting material concentration, the amount of oxidizing agent and the reaction time.

Preferably, the method of the present invention further comprises one or more of the following steps:

d) stopping the reaction of step c), preferably by adding ethylene glycol;

e) purifying the modified hyaluronic acid derivative, preferably by precipitating the modified hyaluronic acid derivative in an organic solvent, preferably ethanol, isopropanol or a mixture thereof, re-dissolving the precipitate in saline and re-precipitating the modified hyaluronic acid derivative in said organic solvent;

f) drying the modified hyaluronic acid derivative obtained in step e).

Preferably, the glycerol-modified hyaluronic acid has a weight average molecular weight of 0.1 to 5.0 MDa, more preferably 1.0 to 3.0 MDa, more preferably 1.0 to 2.0 MDa, even more preferably 1.1 to 1.9, even more preferably 1.2 to 1.8 MDa, even more preferably 1.3 to 1.7 MDa, even more preferably 1.4 to 1.6 MDa. The glycerol-modified hyaluronic acid may also have a weight average molecular weight of 2.0 to 5.0 MDa, or 2.5 to 5.0 MDa, or 3.0 to 5.0 MDa, or 3.0 to 4.5 MDa, or 3.0 to 4.0 MDa.

Also preferably, the glycerol-modified hyaluronic acid has degree of modification of 5 to 25%, preferably 10 to 20%. In this case, the degree of modification is defined as the number of $—CH_2—O—CH_2—CHOH—CH_2OH$ groups divided by the total number of N-acetyl-D-glucosamine units present in the glycerol-modified hyaluronic acid. For example, a MoD of 25.0% means that the glycerol-modified hyaluronic acid contains 25 $—CH_2—O—CH_2—CHOH—CH_2OH$ groups per 100 N-acetyl-D-glucosamine units. A MoD of 50.0% means that the glycerol-modified hyaluronic acid contains 50 $—CH_2—O—CH_2—CHOH—CH_2OH$ groups per 100 N-acetyl-D-glucosamine units, and so on. It has been shown that that degree of modification is particularly suited for preparing an aldehyde modified hyaluronic acid derivative having the desired (rather low) degree of aldehyde modification for preparing a crosslinked hydrogel for aesthetic applications.

Preferably, step c) is performed at a temperature of 4 to 35° C., more preferably 15 to 35° C., even more preferably 20 to 30° C., even more preferably 20 to 25° C., even more preferably 21 to 23° C., even more preferably about 22° C. It has been shown that these rather low reaction temperatures ensure that the obtained aldehyde modified hyaluronic acid derivative according to the present invention has a suitable degree of modification for preparing hydrogels for aesthetic applications.

It is also preferred that step c) is performed for a duration of 5 to 120 minutes, preferably 5 to 65 minutes, more preferably 10 to 60 minutes, even more preferably 10 to 50 minutes, even more preferably 10 to 40 minutes, even more preferably 10 to 30 minutes, even more preferably 10 to 20 minutes. It has been shown that these rather short reaction times also ensure that the obtained aldehyde modified hyaluronic acid derivative according to the present invention has the "correct" degree of modification for preparing hydrogels for aesthetic applications.

It has been found that the degree of (aldehyde) modification increases with increasing reaction times and the molecular weight of the prepared modified hyaluronic acid derivative slightly decreases with increasing reaction times.

Further, it is preferred that the oxidizing agent, preferably sodium periodate, is present in an amount of 0.01 to 0.5 molar equivalents, preferably 0.01 to 0.3 molar equivalents, more preferably 0.04 to 0.3 molar equivalents, even more preferably 0.04 to 0.1 molar equivalents, based on the molar amount of disaccharide repeating units of the glycerol-modified hyaluronic acid.

It has been found that the degree of (aldehyde) modification increases with increasing amounts of oxidizing agent and the molecular weight decreases with increasing amounts of oxidizing agent.

Further, it is preferred that the glycerol-modified hyaluronic acid is present in an amount of 2 to 50 g/L, preferably 2 to 40 g/L, more preferably 3 to 38 g/L, more preferably 4 to 36 g/L, based on the total reaction volume.

It has been found that the degree of (aldehyde) modification increases with increasing amounts of glycerol-modified hyaluronic acid and the molecular weight decreases with increasing amounts of glycerol-modified hyaluronic acid.

In a third aspect, the present invention relates to a modified hyaluronic acid derivative obtained by the method described in the second aspect.

Also in this aspect, it is preferred that the modified hyaluronic acid derivative contains no other chemical modification than an aldehyde group, preferably an aldehyde group present at the C6 carbon atom of the GlcNac unit and having the structure $—CH_2—O—CH_2—CHO$.

Further, it is preferred that the modified hyaluronic acid derivative obtained by the method described in the second aspect has a degree of modification of 1.0% to 20.0%, more preferably 1.0% to 15.0%, even more preferably 1.0% to 10.0%, even more preferably 1.5% to 10.0%, even more preferably 1.5% to 8.0%, even more preferably 1.8% to 7.0%, even more preferably 2.0% to 6.9%.

Further, it is preferred that the modified hyaluronic acid derivative obtained by the method described in the second aspect has a weight average molecular weight of 0.1 to 2.5 MDa, preferably 0.2 to 1.5 MDa, more preferably 0.4 to 1.3 MDa, even more preferably 0.6 to 1.1 MDa.

Further, it is preferred that the modified hyaluronic acid derivative obtained by the method described in the second aspect comprises at least one disaccharide unit of the following structure

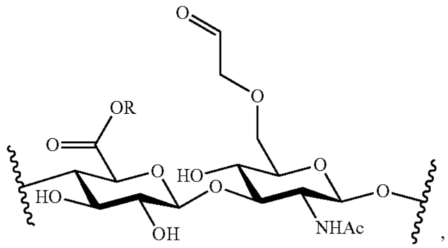
, wherein "Ac" is as defined above and R is selected from hydrogen, an alkali metal ion, preferably Na, or an alkaline earth metal ion. Again, it is to be understood that instead of being present in protonated form (i.e. R=H), the carboxylic acid group can also be present deprotonated form (i.e. R=a negative charge) without any specific counterion being present to balance the negative charge.

Further, the modified hyaluronic acid derivative obtained by the method described in the second aspect may further comprise at least one disaccharide unit of the following structure

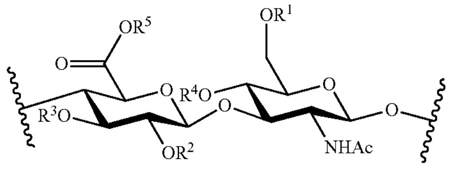
, wherein "Ac" is as defined above and $R^1$, $R^2$, $R^3$ and $R^4$ are independently selected from H and $—CH_2—CHO$ and $R^5$ is selected from hydrogen, an alkali metal ion, preferably Na, an alkaline earth metal ion, and —$CH_2$—CHO, provided that at least one of $R^1$, $R^2$, $R^3$, $R^4$ and $R^5$ is —$CH_2$—CHO and, if $R^1$ is —$CH_2$—CHO, at least one of $R^2$, $R^3$, $R^4$ and $R^5$ is —$CH_2$—CHO.

Further, also in this aspect, it preferred that the number of aldehyde groups present at the C6 carbon atom of the GlcNAc unit (i.e., $R^1$=—$CH_2$—CHO) divided by the total number of aldehyde groups present in the modified hyaluronic acid derivative (including the aldehyde groups present at the C6 carbon atom of the GlcNAc unit) is 0.60 to 1, preferably 0.65 to 1, more preferably 0.70 to 1, even more preferably 0.75 to 1, even more preferably 0.80 to 1, even more preferably 0.85 to 1, even more preferably 0.90 to 1, even more preferably 0.95 to 1, even more preferably 0.97 to 1, even more preferably 0.98 to 1, even more preferably 0.99 to 1, most preferably 1.

In a fourth aspect, the present invention relates to the use of the modified hyaluronic acid derivative of the present invention for the in situ formation of a crosslinked hydrogel in aesthetic applications.

Aesthetic applications of the present invention are non-therapeutic. Preferably, the aesthetic applications of the present invention are non-surgical.

Preferably, the modified hyaluronic acid derivative described in the first and third aspect is used for the in situ formation of a crosslinked hydrogel for treating wrinkles and lines of the skin, including glabellar lines, nasolabial folds, chin folds, marionette lines, jawlines, buccal commissures, perioral wrinkles and crow's feet, cutaneous depressions, scars, temples, subdermal support of the brows, malar and buccal fat pads, tear troughs, nose, lips, cheeks, chin, perioral region, infraorbital region, and facial asymmetries.

In a fifth aspect, the present invention relates to the use of the (aldehyde) modified hyaluronic acid derivative of the present invention or a modified hyaluronic acid derivative obtained by the method of the present invention for the formation of a pre-formed crosslinked hydrogel.

The hydrogel is preferably formed by means of reacting the (aldehyde) modified hyaluronic acid derivative of the present invention with a second polysaccharide derivative, which comprises one or more nucleophilic functional groups capable of forming a covalent with the one or more aldehyde groups. Using the (aldehyde) modified hyaluronic acid derivative of the present invention for preparing a crosslinked hydrogel has various advantages over commonly used BDDE-based production methods. First, since no toxic chemicals are used and preferably only water is produced as by product, less time must be spent for purifying the obtained hydrogel and, therefore, the overall production is much simpler and faster. Further, since the purification is a potential source for contamination, the risk of contamination can substantially be decreased.

Further, since aesthetic applications require a rather low viscosity hydrogel, it has been found that the prepared pre-formed hydrogel shows good injectability through fine needles. If, however, the injection force should be decreased, uncrosslinked polysaccharide, preferably hyaluronic acid, can be added as a lubrication phase.

The hydrogel is preferably formed in a buffer medium, preferably a physiological buffer, more preferably phosphate buffer or citrate buffer or acetate buffer, even more preferably phosphate buffer. Preferably, the buffer is present in an artificial container.

In a sixth aspect, the present invention relates to a modified hyaluronic acid derivative of the present invention for use in the in situ formation of a crosslinked-hydrogel for therapeutic applications, preferably for treating stress urinary incontinence, vaginal dryness, vesico-ureteral reflux, vocal fold insufficiency, and vocal fold medialization.

Preferably, and this applies for all aspects using a hydrogel prepared from the aldehyde modified hyaluronic acid derivative according to the present invention, the modified hyaluronic acid derivative is used together with a second polysaccharide derivative, which comprises one or more nucleophilic functional groups capable of forming a covalent bond with one or more aldehyde groups of the modified HA derivative.

Preferably, and this applies for all aspects using the second polysaccharide derivate, the second polysaccharide derivate is derived from a natural polysaccharide or a semi-synthetic polysaccharide. Specific examples of suitable polysaccharides include cellulose, dextran, starch, alginate, hyaluronic acid, pectin, chitin, chondroitin sulfate, dermatan sulfate, heparin, heparin sulfate, heparosan, and the like.

It is particularly preferred that the second polysaccharide derivate is a hyaluronic acid derivative. In this case, the nucleophilic functional group is preferably attached to the hyaluronic acid backbone via the carboxylic acid group of the D-glucuronic acid moiety.

Preferably, the nucleophilic functional group capable of forming a covalent bond with one or more aldehyde groups of the modified HA derivative is an amino, aminooxy, carbazate or hydrazide moiety, and is preferably a hydrazide moiety.

The term "hydrazide moiety", as used herein, includes a hydrazide functional group and hydrazide-terminated groups or residues, usually having no more than a total number of carbon atoms of 15, 10, 5, 4, 3 or 2. The hydrazide moiety is preferably hydrazide (i.e. [polysaccharide]-C(O)—NH—$NH_2$) or a dihydrazide moiety, particularly a dihydrazide moiety of general formula $$\text{[polysaccharide]-C(=O)—NH—NH—}R^1\text{—C(=O)—NH—}NH_2$$

wherein $R^1$=a covalent bond, C(═O), C(═O)—O—$R^2$, (C═O)—$R^2$, wherein $R^2$=linear or branched $C_1$, $C_2$, $C_3$, $C_4$, $C_5$ or $C_6$ alkyl or alkenyl group. Particularly preferred for use herein is carbodihydrazide (CDH). If CDH is used as hydrazide moiety and coupled with the carboxyl group of a polysaccharide, the resultant modified polysaccharide has the following pendant hydrazide-terminated moiety: polysaccharide-C(═O)—R, wherein R is —NH—NH—C(═O)—NH—$NH_2$.

Preferably, the nucleophilic functional group of the second polysaccharide derivative is attached to the polysaccharide backbone via a free carboxylic acid group of the polysaccharide from which the second polysaccharide derivative is derived. The modification of the carboxylic acid group may be carried out by any method known in the art using a water soluble coupling reagent. For example, a suitable method involves the use of standard carbodiimide chemistry, such as the use of EDC (1-ethyl-3-(3-dimethylaminopropyl) carbodiimide) as coupling reagent, for coupling a hydrazide-terminated moiety with the carboxyl group to form the corresponding polysaccharide acyl hydrazides (see, e.g., WO 95/15168). Other usable coupling reagents are triazine compounds such as DMTMM (4-(4,6-dimethoxy-1,3,5-triazin-2-yl)-4-methylmorpholinium chloride; see, e.g., WO 2016/097211), active esters such as N,N'-disuccinimidyl carbonate, and tetramethyl aminium salts (e.g., HATU).

Preferably, the second polysaccharide is a hyaluronic acid derivative comprising at least one disaccharide unit having the following structure:

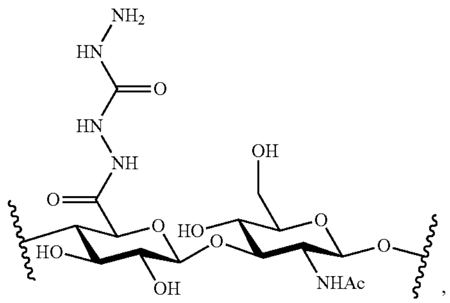

wherein "Ac" is as defined above.

When contacted with each other, the aldehyde group of the modified hyaluronic acid derivative and the nucleophilic functional group of the second polysaccharide derivative spontaneously form a covalent bond upon co-injecting the modified hyaluronic acid derivative and the second polysaccharide derivative to a target site in the body of a subject, thereby forming a crosslinked hydrogel at the target site. Alternatively, the aldehyde group of the modified hyaluronic acid derivative and the nucleophilic functional group of the second polysaccharide derivative spontaneously form a covalent bond upon contacting the same in vitro. In this case, the modified hyaluronic acid derivative and the second polysaccharide are preferably present in a buffer as defined above, wherein the buffer is preferably present in an artificial container.

In a seventh aspect, the present invention relates to a crosslinked hydrogel, comprising the following structural unit:

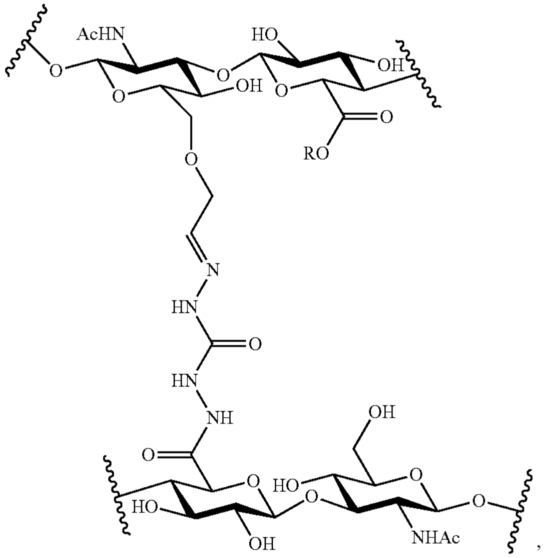

wherein "Ac" denotes —C(O)$CH_3$ and R is selected from hydrogen, an alkali metal ion, preferably Na, and an alkaline earth metal ion.

According to a preferred embodiment, the crosslinked hydrogel is a pre-formed crosslinked hydrogel. Preferably, said pre-formed hydrogel is present in a ready-to-use delivery system, such as a pre-filled syringe. Preferably, said pre-formed crosslinked hydrogel is sterile and ready for being injected into a patient's body, preferably for aesthetic applications. The hydrogel is preferably sterilized by moist heat (e.g., autoclaving). Preferably, the hydrogel is first filled into a delivery system, e.g. a syringe, and the resulting ready-to-use delivery system, such as a pre-filled syringe, is then subjected to sterilization. Preferably, said pre-formed crosslinked hydrogel further comprises uncrosslinked polysaccharide, preferably hyaluronic acid, as lubrication phase. That lubrication phase lowers the injection force through fine needles as commonly used in aesthetic applications and ensures that the hydrogel, although being present in crosslinked form, can be injected through fine needles. Preferably, the uncrosslinked polysaccharide is present in an amount of 1% to 30 wt. %, based on the total amount of polysaccharide, more preferably 5 wt. % to 20 wt. %, even more preferably 7 wt. % to 15 wt. %, even more preferably 8 wt. % to 12 wt. %, even more preferably 9 wt. % to 11 wt. %, even more preferably about 10 wt. %. Also preferably, said pre-formed crosslinked hydrogel further comprises local anesthetic agents, preferably lidocaine, polyalcohols (also referred to as polyols), vitamins, alkali metal and alkaline earth metal salts, metals, antioxidants, amino acids, and ceramic particles anesthetic, preferably lidocaine. Preferably, the local anesthetic agent is present in an amount of 0.05 wt. % to 2 wt. %, based on the total weight of polysaccharide, more preferably 0.1 wt. % to 1 wt. %, even more preferably 0.1 wt. % to 0.8 wt. %, even more preferably 0.1 wt. % to 0.6 wt. %, even more preferably 0.1 wt. % to 0.4 wt. %, even more preferably 0.2 wt. % to 0.4 wt. %, even more preferably about 0.3 wt. %. Preferably, the polyol is present in an amount of 0.5 wt. % to 5.0 wt. %, more preferably 1.0 wt. % to 3.0 wt. %, even more preferably 1.5 wt. % to 2.5 wt. %, even more preferably 1.8 wt. % to 2.2 wt. %, even more preferably about 2.0 wt. %. The polyol is preferably mannitol.

In an eighth aspect, the present invention relates to a crosslinked hydrogel obtained by contacting the modified hyaluronic acid derivative of the present invention and a second polysaccharide derivative as defined above, wherein the crosslinked hydrogel preferably comprises the following structural unit:

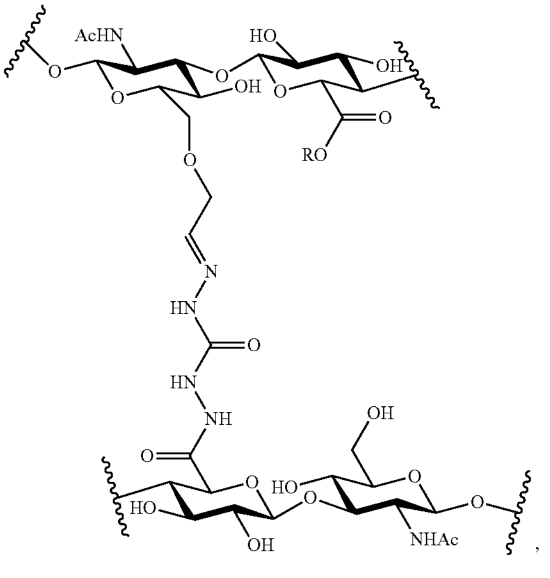

wherein "Ac" denotes —C(O)$CH_3$ and R is selected from hydrogen, an alkali metal ion, preferably Na, and an alkaline earth metal ion.

Preferably, the crosslinked hydrogel described in the seventh and eighth aspect has a storage modulus at 1 Hz of 50 to 1000 Pa, more preferably 50 to 500 Pa, even more preferably 50 to 300 Pa, even more preferably 50 to 150 Pa or 150 to 300 Pa. The storage modulus may be determined by means of rheological measurements conducted at 25° C. at an oscillatory stress of 1 Pa using a frequency scan of 0.1 to 10 Hz.

According to one embodiment, the contacting is performed in situ, i.e. inside a patient's body. According to another embodiment, the contacting is performed in vitro, i.e. outside a human or animal body, preferably in a buffer medium as defined above. Preferably, the buffer medium is located in an artificial container.

In a ninth aspect, the present invention relates to a method, preferably an aesthetic method, of preparing a crosslinked hydrogel. The method comprises the following steps: a) providing a first precursor solution comprising a modified hyaluronic acid derivative of the present invention and separately thereof a second precursor solution comprising a second polysaccharide derivative as described above; b) mixing the first precursor solution and the second precursor solution into an in situ crosslinkable mixture; and c) injecting the in situ crosslinkable mixture to a target site in the body of a patient to form a crosslinked gel at the target site.

Preferably, the first precursor solution and the second precursor solution provided in step a) are sterile.

The term "sterilized" or "sterile", as used herein, is intended to refer to heat sterilization, in particular moist heat sterilization (e.g., steam sterilization), and preferably refers to autoclaving. Autoclaving may be carried out at a temperature of 120° C. to 132° C. for 0.3 min to 20 min, or at 121° C. to 130° C. for 0.5 min to 10 min, e.g. at 121° C. for 0.5 min to 2 min.

The in situ cross-linkable mixture obtained in step b) is easily injectable through thin needles with low injection forces and provides, e.g., skin improvement, skin shaping or good volumizing effect. This advantageously allows the use of fine needles which in turn enhances patient comfort (reduced pain upon injection, lowered back pressure) and further enables the practitioner to accurately and safely (no vessel clogging) inject the hydrogel into the desired target sites, such as various layers of the skin.

The mixing and injection may be achieved using a double-barrel syringe as described herein below or any other suitable syringe system in which the first and second precursor solutions are physically separated prior to simultaneous extrusion and concomitant mixing and injection of the in situ crosslinkable mixture through a needle (or cannula) in the body of a patient. Thus, the co-injection should be as fast as to avoid preliminary cross-linking prior to deposition of the in situ crosslinkable mixture at the target site in the body. On the other hand, the gelling time should be reasonably short in order to avoid spreading of the in situ crosslinkable mixture into surrounding tissues.

Thus, preferably, in step a) the first and second precursor solutions are present in different barrels of a multi-barrel syringe, preferably a double-barrel syringe, and mixing of step b) occurs during extrusion from said multi-barrel syringe.

The term "multi-barrel syringe", as used herein, is intended to mean a syringe, which comprises at least two separate barrels and may have two or more plungers. The term "double-barrel syringe system", as used herein, is intended to mean any system or device, usually a syringe, which comprises two separate barrels and may have one or two plungers. In addition, the multi-barrel, e.g. double-barrel, syringe system generally comprises a tip cap, or a needle or cannula with or without a needle shield, in order to seal the end(s) of the syringe system. The barrels generally have the storage capacity for containing enough of the first and second precursor solutions. The barrels may be made of glass, plastic or any other suitable material and may have different geometries, inner diameters, material compositions, clearness, etc. Further, the multi-barrel syringe system may be a double-barrel syringe system in the form of a syringe having two integrally connected syringes, i.e. two integrally connected barrels, and a mono or double plunger assembly for dispensing the contents from the barrels. Also, the syringe system may include two detachably connected barrels and two or one detachably connected plungers.

Further, the first precursor solution and/or the second precursor solution may comprise additional substances such as cells, including stem cells, and adipocytes, fat, lipids, growth factors, cytokines, drugs, and bioactive. More specifically, the first precursor solution and/or second precursor solution may comprise local anesthetic agents, polyalcohols (also referred to as polyols), vitamins, alkali metal and alkaline earth metal salts, metals, antioxidants, amino acids, and ceramic particles.

Within the context of the present invention, the addition of a local anesthetic is particularly desirable in view of its ability to mitigate pain upon injection. Exemplary local anesthetic agents include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octocaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof.

Preferably, the anesthetic agent is lidocaine, such as in the form of lidocaine HCl. The first and/or second precursor solutions may have a lidocaine concentration of, for example, 0.05 wt. % to 8.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

Suitable polyols for use herein include, but are not limited to, glycerol, mannitol, sorbitol, propylene glycol, erythritol, xylitol, maltitol, and lactitol. Particularly suitable for use herein is mannitol and glycerol. Further, the polyol is preferably glycol, optionally in combination with one or more of the aforementioned polyol compounds, in particular mannitol. Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The vitamins may be present to stimulate and maintain cellular metabolism and, thus, to promote collagen production. Particularly preferred for use here is vitamin C, vitamin E and vitamin $B_6$. A preferred salt for use in the soft tissue filler composition is a zinc salt. The ceramic particles are preferably hydroxyapatite particles, e.g., calcium hydroxyl apatite (CaHA) particles.

Alternatively, the first precursor solution consists of the modified hyaluronic acid derivative and/or the second precursor solution consists of the second polysaccharide derivative.

Also, the first precursor solution may consist of the modified hyaluronic acid derivative and an aqueous buffer solution and/or the second precursor solution may consist of the second polysaccharide derivative and an aqueous buffer solution.

The amount of the modified hyaluronic acid derivative present in the first precursor solution may be from 0.1 wt. % to 5.0 wt. %, preferably from 0.5 wt. % to 4.0 wt. %, more preferably from 1.0 wt. % to 3.0 wt. %, and most preferably from 1.5 wt. % to 2.5 wt. %, and the amount of the second polysaccharide derivative present in the second precursor solution may be from 0.1 wt. % to 5.0 wt. %, preferably from 0.5 wt. % to 4.0 wt. %, more preferably from 1.0 wt. % to 3.0 wt. %, and most preferably from 1.5 wt. % to 2.5 wt. %. Moreover, the weight ratio of the co-injected modified hyaluronic acid derivative and second polysaccharide derivative is preferably from 15:85 to 85:15, more preferably from 30:70 to 70:30, and most preferably 40:60 to 60:40 or 50:50 (modified hyaluronic acid derivative to second polysaccharide derivative).

The first and second precursor solutions typically have a low complex viscosity of 0.001 Pa·s to 5.0 Pa·s, in particular 0.005 Pa·s to 3.0 Pa·s, preferably 0.01 Pa·s to 2.0 Pa·s, more preferably 0.1 Pa·s to 1.8 Pa·s, as determined by oscillatory rheological measurements at 1 Hz and 25° C. Furthermore, the first and second precursor solutions may both be characterized by a low extrusion force of from 0.01 N to 15 N, preferably 0.1 N to 10 N, more preferably 0.5 N to 7.5 N, and most preferably 0.01 N to 50 N or 1.0 N to 5.0 N, as measured through a 30 G needle (TSK Laboratory) at an extrusion rate of about 0.21 mm/see using a standard 1.0 ml glass syringe (BD Hypak SCF, 1 ml long RF-PRTC, ISO 11040, inner diameter of 6.35 mm).

The in situ crosslinkable mixture preferably has a complex viscosity of 0.1 Pa·s to 100 Pa·s, or 0.1 Pa·s to 75 Pa·s, or 1.0 Pa·s to 75 Pa·s, more preferably from 1 Pa·s to 50 Pa·s or from 5 Pa·s to 50 Pa·s, when measured as described above. Furthermore, the injection force of the composition is preferably 0.01 N to 20 N or 0.01 to 10 N, more preferably 0.1 N to 10 N, and most preferably 1.0 N to 5.0 N, when measured as described above.

The in situ crosslinkable mixture that enters the body of a patient, i.e. the mixture of the two precursor solutions, preferably contains a total amount of the modified hyaluronic acid derivative and the second polysaccharide derivative of from 0.1 wt. % to 5.0 wt. %.

In accordance with the present invention, the total amount of hydrazide and aldehyde functionalized HA derivatives present in the liquid composition is preferably from 0.1 wt. % to 5.0 wt. %, in particular from 0.5 wt. % to 4.0 wt. %, more preferably from 1.0 wt. % to 3.0 wt. %, and most preferably from 1.5 wt. % to 2.5 wt. %. Further, the modification ratio of the hydrazide functionalized HA derivative to the aldehyde functionalized HA derivative is preferably from 15:85 to 75:25, more preferably from 25:75 to 60:40, particularly preferable from 40:60 to 60:40, and is most preferably 50:50.

The injected in situ crosslinkable mixture rapidly and efficiently crosslinks in situ to form a covalently crosslinked hydrogel at the target site in the body. No additives, no catalysts, no pH switch, no UV irradiation nor any other external stimuli (or "triggers") are required to induce the crosslinking reaction. In particular, no crosslinker is used or required. The only by-product generated by the crosslinking reaction is typically water that is readily absorbed by the hydrogel and/or the surrounding tissues.

Furthermore, the in situ formed crosslinked hydrogel exhibits favorable mechanical, chemical and rheological properties for use as a soft tissue filler material. In particular, it has a high capacity to create volume. Also, the in situ crosslinked hydrogel of the present has a prolonged in vivo residence time while still being bio-degradable. In addition, it can be desirably include anesthetics (e.g., lidocaine) and a variety of other components (e.g., cells, including stem cells and adipocytes, fat, lipids, growth factors and vitamins). Therefore, the in situ cross-linkable composition of the present invention is particularly suited for use as a dermal filler for aesthetic purposes.

In a tenth aspect, the present invention relates to a method of preparing a crosslinked hydrogel. It is to be understood that the method is performed outside a human or animal body. Or in other words: The crosslinked hydrogel prepared by the method is a pre-formed crosslinked hydrogel. The method comprises the following steps:

Step a): Providing a buffer as defined above.

Step b): Adding the modified hyaluronic acid derivative according to the present invention (or prepared according to the method of the present invention) and adding a second polysaccharide derivative as defined above to the buffer. The modified hyaluronic acid derivative and the second polysaccharide derivative may be added simultaneously or successively in any possible order to the buffer. Optionally, uncrosslinked polysaccharide, preferably hyaluronic acid, may be added to the buffer in step b). The uncrosslinked polysaccharide may also be added simultaneously with or subsequent to any one of the modified hyaluronic acid derivative and the second polysaccharide derivative.

Step c): Crosslinking the modified hyaluronic acid derivative and the second polysaccharide derivative in the buffer to thereby prepare a crosslinked gel.

Step d): Optional addition of uncrosslinked polysaccharide as defined above.

Step e): Optional sieving and degassing of the hydrogel obtained in step c) or d).

Step f): Optional filling of the hydrogel obtained in step c), d), or e) in a container, preferably a syringe, more preferably a ready-to-use syringe.

Step g): Optional sterilizing of the container comprising the gel obtained in step f).

Preferably, step d) is part of the method. Also preferably, steps e), f), and g) are part of the method. More preferably, steps d), e), f), and g) are part of the method.

The inventive method of preparing a crosslinked hydrogel is highly advantageous over a BDDE-based method of preparing a crosslinked hydrogel. In particular, the inventive method is significantly simpler and less error prone. That is because, while a BDDE-based method for preparing a hydrogel comprises the following general steps:

1. HA dissolution
2. Addition of BDDE
3. Crosslinking reaction at elevated temperature
4. Neutralization
5. Filling into dialysis tubes
6. Dialysis against buffer (e.g. PBS)
7. Adjustment of gel concentration and addition of additives (e.g. lubrication phase, lidocaine etc.)

8. Sieving and degassing
9. Filling into syringe
10. Sterilization the inventive method only comprises the following general steps:

1. Dissolution of both components in a buffer
2. Addition of lubrication phase, if any
3. Wait (crosslinking reaction at only room temperature)
4. Sieving and degassing
5. Filling into syringe
6. Sterilization.

Thus, the inventive method comprises a significantly lower number of process steps, which renders the inventive step much simpler, faster, and, thus, cheaper. Further, since the relatively error-prone purification by means of dialysis can be avoided in the inventive method, the inventive method shows a significantly lower risk of contamination. Further, since no harmful BDDE is required in the inventive method, the inventive method poses less health and environmental risks.

It has been found that the properties, in particular the rheological properties, of the gel can be fine-tuned by means of the degree of modification of the modified hyaluronic acid derivative (and also the second polysaccharide derivative). Further, the properties, in particular the rheological properties, of the gel can be fine-tuned by means of adjusting the polymer concentrations in the buffer. In general, a high polymer concentration leads to a high storage modulus (G') of a prepared crosslinked hydrogel. Preferably, the concentration of the modified hyaluronic acid derivative of the present invention in the buffer is 1 g/L to 40 g/L, more preferably 2 g/L to 30 g/L, even more preferably 5 g/L to 25 g/L, even more preferably 10 g/L to 25 g/L, even more preferably 12 g/L to 25 g/L, even more preferably 15 g/L to 25 g/L. Preferably, the concentration of the second polysaccharide derivative in the buffer is 1 g/L to 40 g/L, more preferably 2 g/L to 30 g/L, even more preferably 5 g/L to 25 g/L, even more preferably 10 g/L to 25 g/L, even more preferably 12 g/L to 25 g/L, even more preferably 15 g/L to 25 g/L.

Preferably, crosslinking in step c) is performed for 1 hour to 24 hours, more preferably for 2 hours to 20 hours, even more preferably for 2 hours to 18 hours, even more preferably for 2 hours to 16 hours, even more preferably for 3 hours to 16 hours, even more preferably 4 hours to 15 hours, even more preferably 4 hours to 14 hours, even more preferably 5 hours to 12 hours, even more preferably 6 hours to 10 hours, even more preferably 7 hours to 9 hours, even more preferably about 8 hours.

Preferably, crosslinking in step c) is performed at a temperature of 20° C. to 35° C., more preferably at 20° C. to 30° C., even more preferably at 20° C. to 25° C.

According to a preferred embodiment, the uncrosslinked polysaccharide is added in step b). According to another preferred embodiment, the uncrosslinked polysaccharide is added in step d). According to another preferred embodiment, the uncrosslinked polysaccharide is added in steps b) and d). Preferably, the uncrosslinked polysaccharide is added in step b) and/or step d) such that it is present at a final concentration of 1 wt. % to 30 wt. %, based on the total amount of polysaccharide, more preferably 5 wt. % to 20 wt. %, even more preferably 7 wt. % to 15 wt. %, even more preferably 8 wt. % to 12 wt. %, even more preferably 9 wt. % to 11 wt. %, even more preferably about 10 wt. %.

In an eleventh aspect the present invention relates to a kit for the in situ formation of a crosslinked hydrogel, comprising (i) a first container containing the first precursor solution as described above and (ii) a second container containing the second precursor solution as described above.

It is understood that the various embodiments of the first and second precursor solutions described above also apply for this aspect. This includes, e.g., that the first and second precursor solutions are preferably present in different barrels of a multi-barrel syringe, preferably a double-barrel syringe. The system of a multi-barrel syringe comprising the first and second precursor solutions in different barrels may also be denoted as a "delivery system".

The kit may further comprise instructions for use.

The term "container" is not particularly limited and includes, for example, glass or plastic bottles, vials, carpules, or any other sealed container.

The "instructions for use" are preferably instructions for use in aesthetic or therapeutic applications, in particular replacing or filling of a biological tissue or increasing the volume of a biological tissue for the purpose of aesthetic or therapeutic applications, as defined herein or, particularly preferred, instructions for use as a dermal filler in aesthetic uses.

The present invention will now be further illustrated by the following, non-limiting examples.

EXAMPLES

Chemicals

The chemicals used in the context of the present invention were obtained from the following suppliers and used without further purification:

| Material | Supplier |
|---|---|
| Glycerol-modified HA (Mw = 1.4 MDa, MoD = 10-20%) | HTL Biotechnology |
| HA | HTL Biotechnology |
| Hydrazide-modified HA | Merz Pharmaceuticals GmbH |
| | Synthesized according to D'Este et al., |

-continued

| Material | Supplier |
|---|---|
| 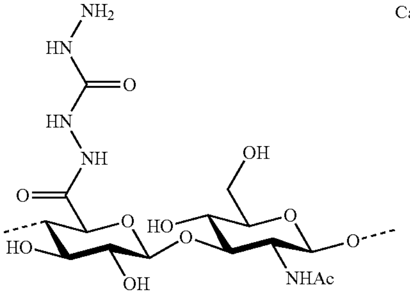 | Carbohydr. Polym. 2014, 108:239-246 |
| Sodium periodate | Merck |
| Ethylene glycol | Sigma Aldrich |
| NaCl | Merck |
| Ethanol (denatured with 1% methyl ethyl ketone) | VWR |
| Purified Water | Merz GmbH & Co. KGaA |
| Tyrosine hydrazide | Sigma Aldrich |

Equipment

The following laboratory equipment was used in the context of the present invention:

| Equipment | Description |
|---|---|
| Purified water system | ELIX 20 |
| Diverse lab equipment | Balance, beakers, stirrers, pipettes |
| Vacuum Oven | Memmert VO400 |
| Rheometer | Anton Paar Physica MCR 302 Rheometer |
| Autoclave | Systec HX 150 |

General Procedure for Synthesis of Aldehyde-Modified Hyaluronic Acid Derivative of the Present Invention Glycerol-modified HA (in a form of powder or fibers) is weighed-in, required amount of a solvent (purified water or buffer) is added and the mixture is stirred in order to obtain a homogeneous polymer solution. Thereafter, an oxidizing agent (sodium periodate) is added and the solution is stirred vigorously for the desired amount of time. In order to stop the reaction a quenching agent (e.g. a vicinal diol (1,2-diol), preferably ethylene glycol) is added, followed by the addition of NaCl. Purification is carried out by pouring the reaction mixture in an organic solvent (e.g. ethanol or isopropanol). The precipitate is collected and dissolved once again in saline, followed by a second precipitation in the organic solvent (e.g. ethanol). The product is collected, rinsed with the organic solvent (e.g. ethanol) and dried under vacuum for a certain time (e.g. overnight).

Characterization

1. Molecular Weight

Molecular weight of the material was determined by using size exclusion chromatography coupled with a multi-angle light scattering detector, a refractive index detector, and a viscometer. A sample was prepared by dissolving 2 mg of dried modified HA in 10 mL PBS buffer over a period of 4 h at 25° C. resulting in a concentration of 0.2 mg/mL. The sample solution was filtered through a 0.45 μm filter into a 1.8 mL vial for chromatography. Thereafter, 50 μL of this solution was injected in the system (eluent PBS buffer, flow rate 0.7 mL/min, column temperature 35° C.). An exemplary chromatogram is shown in FIG. 1.

2. Degree of Modification

Figure 2:
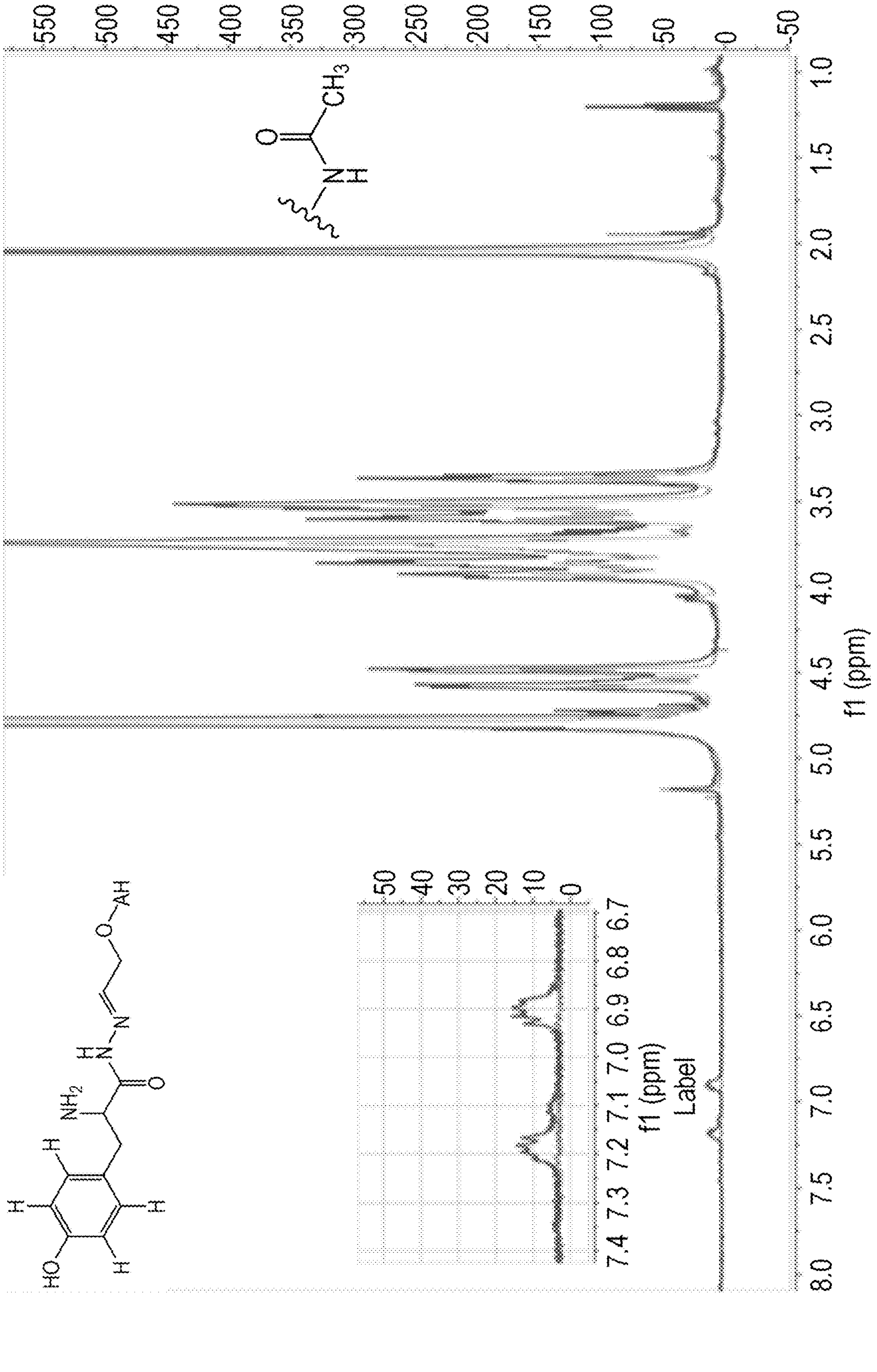
FIG. 2 shows an exemplary 1H NMR spectrum of tyrosine labelled aldehyde-modified hyaluronic acid derivative.

The degree of modification of the aldehyde-modified hyaluronic acid derivative of the present invention was measured by using $^1H$ NMR. Namely, the prepared aldehyde-modified hyaluronic acid derivative was first labelled with tyrosine hydrazide: 66 mg of the aldehyde-modified hyaluronic acid derivative were dissolved in 15 mL water, followed by the addition of 88 mg of tyrosine hydrazide. The reaction took place 20 hours and then 150 mg NaCl were added. The reaction mixture was precipitated in 75 mL of ethanol. The precipitate was collected and dissolved in saline solution (150 mg NaCl in 15 mL water). Precipitation in ethanol was carried out once again. The solid was collected and dried under vacuum. The labelled aldehyde-modified hyaluronic acid derivative was thereafter treated for 1H NMR measurement by digesting 20 mg of the material with 300 units hyaluronidase at 40° C. overnight. Thereafter, MoD is determined by comparing the peak area at around 6.9 ppm (aromatic protons from tyrosine hydrazide) with the peak area at around 2.0 ppm ($—CH_3$ protons in the polymer backbone). An exemplary 1H NMR spectrum of tyrosine labelled aldehyde-modified hyaluronic acid derivative is shown in FIG. 2.

Example 1 (Influence of Concentration of Starting Material (Glycerol-Modified HA) on Molecular Weight and MoD of Aldehyde-Modified Hyaluronic Acid Derivative)

The reaction was performed according to the general procedure described above. The reaction time was kept constant at 10 min, 0.1 eq. of $NaIO_4$ was applied and the reaction was carried out at 22° C. The concentration of the glycerol-modified HA was varied. The influence of the glycerol-modified HA on the properties of the prepared materials is shown in the following table:

| Example | c (glycerol-modified HA)/g $L^{-1}$ | MoD/% | Mw/MDa |
|---|---|---|---|
| 1.1 | 4 | 2.1 | 1.1 |
| 1.2 | 12 | 4.5 | 0.9 |
| 1.3 | 24 | 5.7 | 0.7 |
| 1.4 | 36 | 6.1 | 0.6 |

Example 1.1

1.49 g glycerol-modified HA (Loss on Drying (LoD) was 6.2%) were weighed-in, followed by the addition of 315 g of water and the mixture was stirred for 16 h at 22° C. to obtain a homogeneous solution. Thereafter, 0.074 g (0.35 mmol) of sodium periodate dissolved in 35 g of water were added and the mixture was vigorously stirred for 10 min at 22° C. In order to stop the oxidation 3.9 mL (69 mmol) of ethylene glycol were added fast. Thereafter, 1.75 g NaCl were added under stirring until a homogeneous mixture was obtained and the solution was precipitated in 1.75 L of ethanol. The polymer was collected, placed in a fresh dish, 1.75 g NaCl were added and they were dissolved in 350 mL water. The homogeneous mixture was poured in 1.75 L of fresh ethanol, solid was collected and the product was dried under vacuum to obtain white fibers. Material properties: MoD of 2.1% (mol/mol) and Mw of 1.1 MDa Example 1.4

13.4 g glycerol-modified HA (LoD was 6.2%) were weighed-in, followed by the addition of 315 g of water and the mixture was stirred for 16 h at 22° C. to obtain a homogeneous solution. Thereafter, 0.663 g (3.1 mmol) of sodium periodate dissolved in 35 g of water were added and the mixture was vigorously stirred for 10 min at 22° C. In order to stop the oxidation 34.7 mL (620 mmol) of ethylene glycol were added fast. Thereafter, 2800 mL water and 16 g NaCl were added, stirred until a homogeneous mixture was obtained and the solution was precipitated in 16 L of ethanol. The polymer was collected, placed in a fresh dish, 16 g NaCl were added and they were dissolved in 3000 mL water. The homogeneous mixture was poured in 16 L of fresh ethanol, solid was collected and the product was dried under vacuum to obtain white fibers. Material properties: MoD of 6.1% (mol/mol) and $M_w$ of 0.6 MDa Example 2 (Influence of Amount of Oxidizing Agent (Sodium Periodate) on Molecular Weight and MoD of Aldehyde-Modified Hyaluronic Acid Derivative)

The reaction was performed according to the general procedure described above. The concentration of glycerol-modified HA in the reaction was kept constant at 12 g/L, reaction time was 10 min and the reaction was carried out at room temperature. The only parameter which was varied was the amount of sodium periodate. Properties of the prepared materials are given in the following table (shown are the equivalents of $NaIO_4$ based on the molar amount of disaccharide repeating units of the glycerol-modified hyaluronic acid):

| Example | eq $NaIO_4$ | MoD/% | Mw/MDa |
|---|---|---|---|
| 2.1 | 0.05 | 2.9 | 1.0 |
| 2.2 | 0.1 | 4.5 | 0.9 |
| 2.3 | 0.15 | 5.9 | 0.8 |
| 2.4 | 0.2 | 6.8 | 0.6 |

Example 2.1

4.48 g glycerol-modified HA (LoD was 6.2%) were weighed-in, followed by the addition of 315 g of water and the mixture was stirred for 16 h at 22° C. to obtain a homogeneous solution. Thereafter, 0.11 g (0.51 mmol) of sodium periodate dissolved in 35 g of water were added and the mixture was vigorously stirred 10 min at 22° C. In order to stop the oxidation 11.6 mL (207 mmol) of ethylene glycol was added. Thereafter, 700 mL water and 5.25 g NaCl was added, stirred until a homogeneous mixture was obtained and the solution was precipitated in 5 L of ethanol. The polymer was collected, placed in a fresh dish, 5.25 g NaCl were added and they were dissolved in 1000 mL water. The homogeneous mixture was poured in 5 L of fresh ethanol, solid was collected and the product was dried under vacuum to obtain white fibers. Material properties: MoD of 2.9% (mol/mol) and Mw of 1.0 MDa Example 2.4

4.48 g glycerol-modified HA (LoD was 6.2%) were weighed-in, followed by the addition of 315 g of water and the mixture was stirred for 16 h at 22° C. to obtain a homogeneous solution. Thereafter, 0.44 g (2.1 mmol) of sodium periodate dissolved in 35 g of water were added and the mixture was vigorously stirred 10 min at 22° C. In order to stop the oxidation 11.6 mL (207 mmol) of ethylene glycol were added. Thereafter, 700 mL water and 5.25 g NaCl were added, stirred until a homogeneous mixture was obtained and the solution was precipitated in 5 L of ethanol. The polymer was collected, placed in a fresh dish, 5.25 g NaCl was added and they were dissolved in 1000 mL water. The homogeneous mixture was poured in 5 L of fresh ethanol, solid was collected and the product was dried under vacuum to obtain white fibers. Material properties: MoD of 6.8% (mol/mol) and Mw of 0.6 MDa Example 3 (Influence of Reaction Time on Molecular Weight and MoD of Aldehyde-Modified Hyaluronic Acid Derivative)

The reaction was performed according to the general procedure described above. The concentration of glycerol-modified HA in the reaction was kept constant at 12 g/L, 0.1 eq. of NaIO4 were used and the reaction was carried out at 22° C. The only parameter which was varied was the reaction time. Properties of the prepared materials are given in the following table:

| Example | Reaction time/min | MoD/% | Mw/MDa |
|---|---|---|---|
| 3.1 | 10 | 4.5 | 0.9 |
| 3.2 | 15 | 5.7 | 0.7 |
| 3.3 | 20 | 5.9 | 0.8 |
| 3.4 | 60 | 6.1 | 0.7 |

Example 3.4

4.93 g glycerol-modified HA (LoD was 6.2%) were weighed-in, followed by the addition of 345 g of water and the mixture was stirred for 16 h at 22° C. to obtain a homogeneous solution. Thereafter, 0.22 g (1.0 mmol) of sodium periodate dissolved in 39 g of water were added and the mixture was vigorously stirred 60 min at 22° C. In order to stop the oxidation 12.7 mL (227 mmol) of ethylene glycol were added. Thereafter, 770 mL water and 6 g NaCl was added, stirred until a homogeneous mixture was obtained and the solution was precipitated in 6 L of ethanol. The polymer was collected, placed in a fresh dish, 6 g NaCl was added and they were dissolved in 1100 mL water. The homogeneous mixture was poured in 6 L of fresh ethanol, solid was collected and the product is dried under vacuum to obtain white fibers. Material properties: MoD of 6.1% (mol/mol) and Mw of 0.7 MDa.

Example 4: Application of the Aldehyde-Modified Hyaluronic Acid Derivative for the Preparation of In Situ Hydrogels Hyaluronic acid carrying aldehyde groups can be used for the preparation of in situ cross-linkable hydrogels. Namely, hyaluronic acid sodium salt carrying an aldehyde group (an electrophilic group) can covalently react with a polysaccharide carrying a nucleophilic group (e.g. hydrazide group) to form an in situ cross-linked gel. Depending on the modification degree and on the molecular weight of the aldehyde-modified hyaluronic acid derivative gels with different rheological properties can be obtained. To check the gelation performance of the prepared aldehyde-modified hyaluronic acid derivative, material was dissolved in water or a buffer, filled in glass syringes and sterilized. Similarly, hydrazide-modified hyaluronic acid sodium salt was also dissolved in water or a buffer, filled in syringes and sterilized. Thereafter, the contents of two solutions were mixed and polymers were let to cross-link (chemically react) with each other. Namely, the hydrazide group of one polymer reacted with the aldehyde group of the other material and the gel was formed through the formation of a hydrazone bond (see Scheme below). Prepared gels were characterized by measuring their rheological properties 24 hours after they were mixed. Storage modulus (G') was measured at 25° C. using the rheometer equipped with a cone-plate geometry (50 mm diameter, 0.1° angle, CP50-1, gap size 0.1 mm). The samples were oscillated at a stress of 1 Pa using a frequency scan of 0.1 to 10 Hz, wherein the values indicated are at 1 Hz.

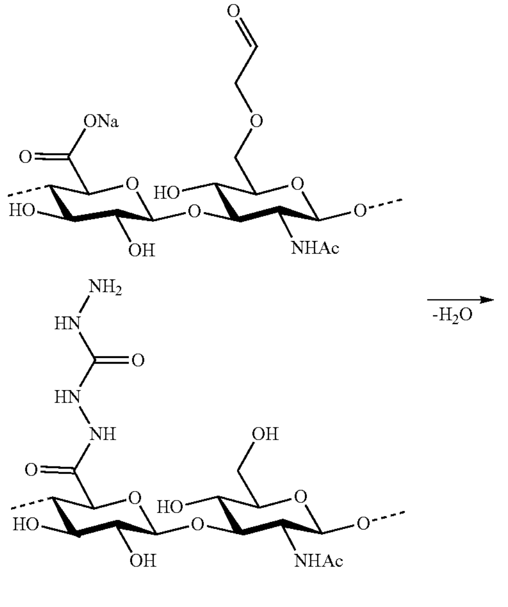

-continued

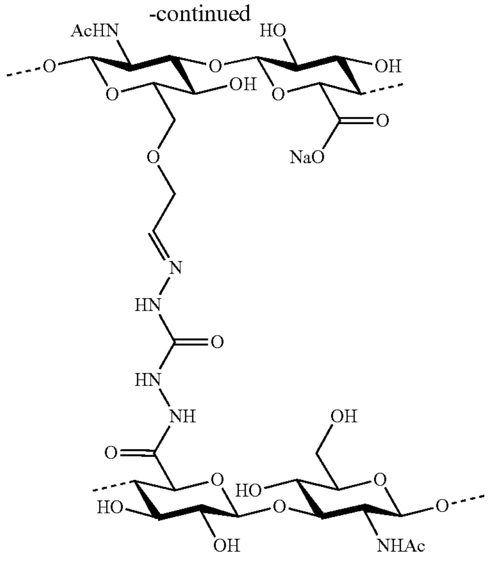

Example 4.1

Aldehyde-modified hyaluronic acid derivative (material from Example 1.1: MoD=2.1%, $M_w$=1.1 MDa) was dissolved in 3 mM phosphate buffer (pH 7), filled in a glass syringe and steam sterilized (127° C., 6.5 min). Hydrazide-modified hyaluronic acid sodium salt (MoD=2.1%, $M_w$=1.3 MDa) was dissolved in 3 mM phosphate buffer (buffer contained 0.6 wt. % lidocaine and had pH 7), filled in a glass syringe and steam sterilized (127° C., 6.5 min). Thereafter, 0.6 g of Aldehyde-modified hyaluronic acid derivative solution was weighed in an empty glass syringe, followed by the addition of the 0.6 g of the hydrazide-modified hyaluronic acid sodium salt solution. The syringe was closed with a plunger stopper, connected to the empty syringe via a luer-lock connector and the content was pushed from one syringe to the other 40 times. Thereafter, the syringe with the content was closed and the crosslinking took part at 22° C. for 24 hours. Thereafter, the rheological properties of the gel were measured. The gel reached a storage modulus of 68 Pa.

Example 4.2

Aldehyde-modified hyaluronic acid derivative (material from Example 2.1: MoD=2.9%, Mw=1.0 MDa) was dissolved in 3 mM phosphate buffer (pH 7), filled in a glass syringe and steam sterilized (127° C., 6.5 min). Hydrazide-modified hyaluronic acid sodium salt (MoD=2.1%, Mw=1.3 MDa) was dissolved in 3 mM phosphate buffer (buffer contained 0.6 wt. % lidocaine and had pH 7), filled in a glass syringe and steam sterilized (127° C., 6.5 min). Thereafter, 0.6 g of an aldehyde-modified hyaluronic acid derivative solution was weighed in an empty glass syringe, followed by the addition of the 0.6 g of the hydrazide-modified hyaluronic acid sodium salt solution. The syringe was closed with a plunger stopper, connected to the empty syringe via a luer-lock connector and the content was pushed from one syringe to the other 40 times. Thereafter, the syringe with the content was closed and the crosslinking took part at 22° C. for 24 hours. Thereafter, the rheological properties of the gel were measured. The gel reached a storage modulus of 164 Pa.

Example 4.3

Aldehyde-modified hyaluronic acid derivative (material from Example 2.4: MoD=6.8%, $M_w$=0.6 MDa) was dissolved in 3 mM phosphate buffer (pH 7), filled in a glass syringe and steam sterilized (127° C., 6.5 min). Hydrazide-modified hyaluronic acid sodium salt (MoD=2.1%, $M_w$=1.3 MDa) was dissolved 3 mM phosphate buffer (buffer contained 0.6 wt. % lidocaine and had pH 7), filled in a glass syringe and steam sterilized (127° C., 6.5 min). Thereafter, 0.6 g of aldehyde-modified hyaluronic acid derivative solution was weighed in an empty glass syringe, followed by the addition of the 0.6 g of the hydrazide-modified hyaluronic acid sodium salt solution. The syringe was closed with a plunger stopper, connected to the empty syringe via a luer-lock connector and the content was pushed from one syringe to the other 40 times. Thereafter, the syringe with the content was closed and the crosslinking took part at 22° C. for 24 hours. Thereafter, the rheological properties of the gel were measured. The gel reached a storage modulus of 277 Pa.

Example 5 (Importance of Using Glycerol-Modified HA in the Oxidation Reaction)

It is known that aldehyde groups can be introduced in the structure of carbohydrates by the oxidation with sodium periodate. However, required reaction times for this synthesis are long and the reaction leads to the significant reduction of the molecular weight of the polymer because the oxidation is happening on the polymer backbone. In order to avoid this, glycerol-modified HA can be used for the oxidation because the pending glycerol unit is more accessible to oxidation than the hydroxyl groups of the HA backbone. To confirm this, native HA and glycerol-modified HA were oxidized under the identical conditions and their properties were tested. Reaction conditions were: polymer concentration: 12 g/L; reaction temperature: 22° C. and 0.1 eq of sodium periodate (in regard to the number of hyaluronic acid repeating unit). Gelation performance of the oxidized native HA and oxidized glycerol-modified HA are given in the following table:

| HA | Reaction time/min | G'/Pa |
|---|---|---|
| glycerol-modified HA | 10 | 138.0 |
| native HA | 10 | 0.3 |
| glycerol-modified HA | 60 | 304.1 |
| native HA | 60 | 0.2 |

The results show that under the mild conditions used for the oxidation of glycerol-modified HA, native HA cannot yield a material which can form a gel when it is mixed with hydrazide-modified hyaluronic acid solution.

Example 6 (Preparation of Pre-Formed Hydrogels)

Two gels with different concentration [10 mg/mL (Ex. 6.1); 20 mg/mL (Ex. 6.2)] were prepared.

Example 6.1

2.5 g of hydrazide-modified HA (average molecular weight of 1.5 MDa and modification degree of 2.1%) and 2.5 g of aldehyde-modified HA (prepared according to the present invention; average molecular weight of 1.1 MDa and modification degree of 4.3%) were weighed in a Kenwood bowl, followed by the addition of 450 mL of 10 mM phosphate buffer (pH 7, containing 2 wt. % mannitol and 0.3 wt. % lidocaine). The mixture was stirred for 8 hours, then 50 mL of a solution containing non-crosslinked HA at a concentration of 10 mg/mL in 10 mM phosphate buffer was added, and thereafter the resulting product was filled into syringes and sterilized at 127° C. for 6.5 minutes. The gel was characterized by measuring the rheological properties (before and after sterilization), extrusion force (after sterilization), pH and osmolality. The obtained data are shown in the following table:

| Product | Polymer concentration/ $mg \cdot mL^{-1}$ | G' before sterilization/ Pa | G' after sterilization/ Pa | Extrusion Force/N (30G TSK needle) | pH | Osmolality/ $mOsm \cdot kg^{-1}$ |
|---|---|---|---|---|---|---|
| Gel prepared in Ex. 6.1 | 10 | 152 | 24 | 28.4 | 6.86 | 341 |

Example 6.2

5.0 g of hydrazide-modified HA (average molecular weight of 1.5 MDa and modification degree of 2.1%) and 5.0 g of aldehyde-modified HA (prepared according to the present invention; average molecular weight of 1.1 MDa and modification degree of 4.3%) were weighed in a Kenwood bowl, followed by the addition of 450 mL of 10 mM phosphate buffer (pH 7, containing 2 wt. % mannitol and 0.3 wt. % lidocaine). The mixture was stirred for 8 hours, then 50 mL of a solution containing non-crosslinked HA at a concentration of 20 mg/mL in 10 mM phosphate buffer was added, and thereafter the resulting product was filled into syringes and sterilized at 127° C. for 6.5 minutes. The gel was characterized by measuring the rheological properties (before and after sterilization), extrusion force (after sterilization), pH and osmolality. The obtained data are shown in the following table:

| Product | Polymer concentration/ mg · $mL^{-1}$ | G' before sterilization Pa | G' after sterilization/ Pa | Extrusion Force/N (27G TSK needle) | pH | Osmolality/ mOsm · $kg^{-1}$ |
|---|---|---|---|---|---|---|
| Gel prepared in Ex. 6.2 | 20 | 823 | 243 | 23.4 | 6.77 | 371 |

As can be seen in Examples 6.1 and 6.2, the properties of the obtained hydrogel can be fine-tuned by simply modifying the polymer concentration.

Example 7 (Thermal Stability of Gels Prepared According to the Inventive Method)

To test the thermal stability of pre-formed gels prepared according to the inventive method, two formulations were prepared and placed in the oven at 40° C. The rheological properties of the gels were investigated at different time points (0, 3, 6, 9 and 12 weeks).

Gel 1:

0.45 g of hydrazide-modified HA (molecular weight of 1.8 MDa and modification degree of 3.7%) were dissolved in a syringe in saline solution containing 0.6 wt. % lidocaine. In a second syringe 0.45 g of aldehyde-modified HA (prepared according to the present invention; molecular weight of 1.2 MDa and modification degree of 3.7%) were dissolved in 30 mL 25 mM PBS buffer (which contained 1.25 g of mannitol).

The syringes containing HA-hydrazide solution and HA-aldehyde solution were connected via a luer-lock connector and their contents were vigorously mixed. Thereafter, the homogeneous mixture was filled in glass BD syringes and sterilized at 127° C. for 6.5 min. The syringes containing gel were placed in the oven at 40° C.

Gel 2:

0.45 g of hydrazide-modified HA (molecular weight of 1.8 MDa and modification degree of 3.7%) were dissolved in a syringe in saline solution containing 0.6 wt. % lidocaine. In a second syringe 0.45 g of aldehyde-modified HA (prepared according to the present invention; molecular weight of 1.2 MDa and modification degree of 3.7%) were dissolved in 30 mL 3 mM PBS buffer (without mannitol).

The syringes containing HA-hydrazide solution and HA-aldehyde solution were connected via a luer-lock connector and their contents were vigorously mixed. Thereafter, mixture was filled in glass syringes and sterilized at 127° C. for 6.5 min. The syringes containing gel were placed in the oven at 40° C.

Figure 3:
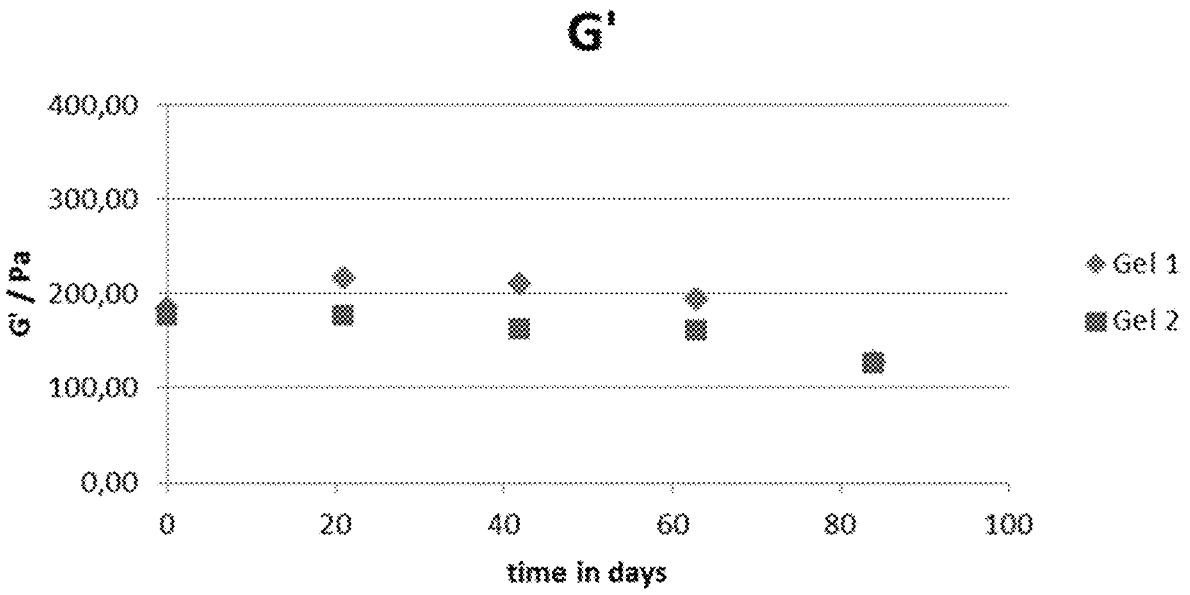
FIG. 3 shows the storage modulus (G') of gels 1 and 2 stored at 40° C.
Figure 4:
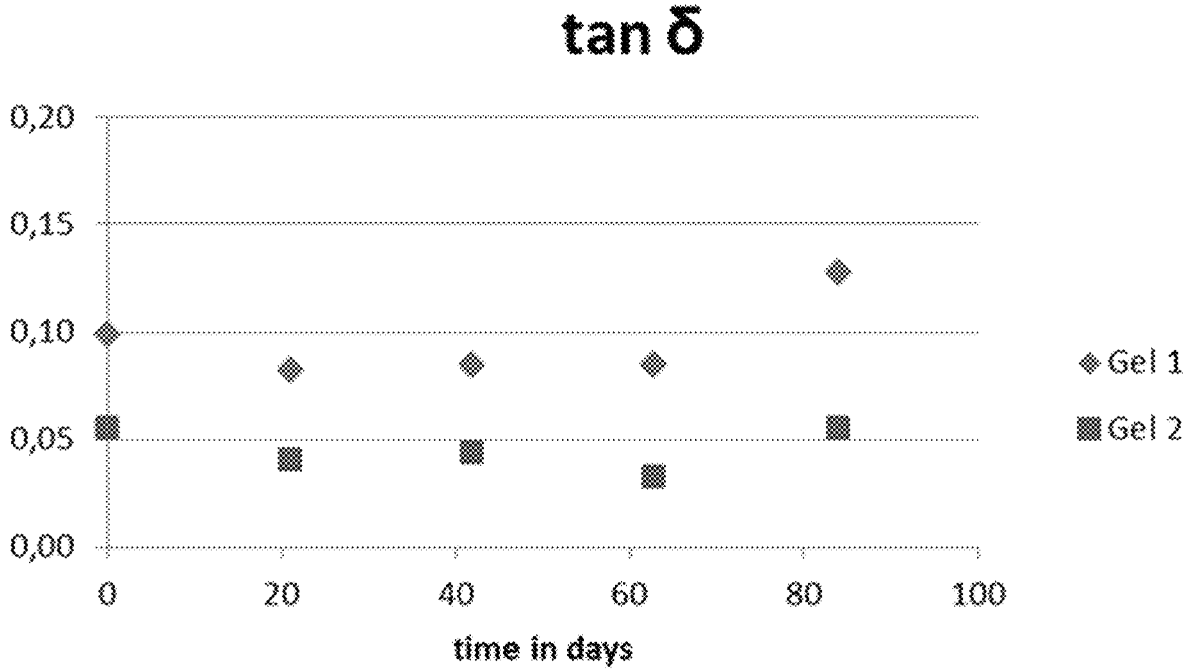
FIG. 4 shows the loss factor (tan δ) of gels 1 and 2 stored at 40° C.

The results are shown in FIGS. 3 and 4. As it can be seen, both gels show similar and good thermal stability.

The invention claimed is:

1. A modified hyaluronic acid derivative, wherein the —$CH_2$—OH group of at least one N-acetyl-D-glucosamine unit is modified into an aldehyde group having a structure —$CH_2$—O—$CH_2$—CHO, wherein the degree of modification is 2.0% to 6.9%, the degree of modification being defined as the number of —$CH_2$—O—$CH_2$—CHO groups divided by the total number of N-acetyl-D-glucosamine units present in the modified hyaluronic acid derivative, wherein the number of aldehyde groups having the structure —$CH_2$—O—$CH_2$—CHO of the at least one N-acetyl-D-glucosamine unit divided by the total number of aldehyde groups present in the modified hyaluronic acid derivative is from 0.95 to 1, wherein the modified hyaluronic acid derivative has a weight average molecular weight of 0.4 MDa to 1.3 MDa, and wherein the modified hyaluronic acid derivative comprises at least one disaccharide unit of the following structure

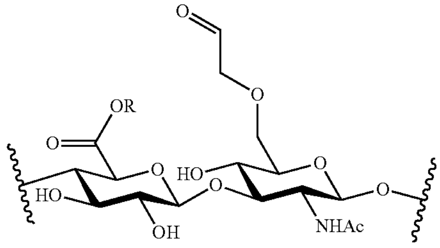

wherein Ac denotes —C(O)$CH_3$ and R is selected from the group consisting of hydrogen, an alkali metal ion and an alkaline earth metal ion, and further comprises at least one disaccharide unit of the following structure

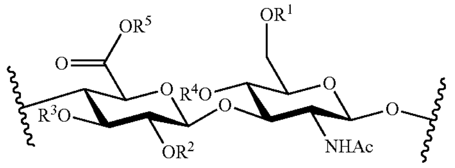

wherein Ac denotes —C(O)$CH_3$, $R^1$, $R^2$, $R^3$ and $R^4$ are independently selected from the group consisting of H and —$CH_2$—CHO, and $R^5$ is selected the group consisting of from hydrogen, an alkali metal ion, an alkaline earth metal ion, and —$CH_2$—CHO, wherein, at least one of $R^1$, $R^2$, $R^3$, $R^4$ and $R^5$ is —$CH_2$—CHO and, if $R^1$ is —$CH_2$—CHO, at least one of $R^2$, $R^3$, $R^4$, and $R^5$ is —$CH_2$—CHO.

2. A method for preparing the modified hyaluronic acid derivative of claim 1, comprising:

a) providing a glycerol-modified hyaluronic acid, wherein a —$CH_2$—OH group of at least one N-acetyl-D-glucosamine unit is modified into a group of the following formula —$CH_2$—O—$CH_2$—CHOH—$CH_2$OH;

b) dissolving the glycerol-modified hyaluronic acid in an aqueous medium to obtain solubilized glycerol-modified hyaluronic acid; and c) reacting said solubilized glycerol-modified hyaluronic acid with an oxidizing agent, optionally a periodate, optionally sodium periodate, to convert at least a part of said —$CH_2$—O—$CH_2$—CHOH—$CH_2$OH groups into one or more aldehyde groups having the formula —$CH_2$—O—$CH_2$—CHO, thereby obtaining an aldehyde-modified hyaluronic acid derivative.

3. The method of claim 2, further comprising one or more of:

d) stopping the reaction of c), optionally by adding a vicinal diol (1,2-diol), optionally ethylene glycol;

e) purifying the modified hyaluronic acid derivative, optionally by precipitating the modified hyaluronic acid derivative in an organic solvent, optionally ethanol, isopropanol or a mixture thereof, re-dissolving the precipitate in saline and re-precipitating the modified hyaluronic acid derivative in said organic solvent; or f) drying the modified hyaluronic acid derivative obtained in e).

4. The method of claim 2, wherein the glycerol-modified hyaluronic acid has a weight average molecular weight of 0.1 to 5.0 MDa, optionally 1.0 to 3.0, optionally 1.0 to 2.0 MDa, optionally 1.1 to 1.9, optionally 1.2 to 1.8 MDa, optionally 1.3 to 1.7 MDa, optionally 1.4 to 1.6 MDa and/or a degree of modification of 5 to 25%, optionally 10 to 20%, the degree of modification being defined as the number of $—CH_2—O—CH_2—CHOH—CH_2OH$ groups divided by the total number of N-acetyl-D-glucosamine units present in the glycerol-modified hyaluronic acid and/or wherein (i) c) is performed at a temperature of 4 to 35° C., optionally 15 to 35° C., optionally 20 to 30° C., optionally 20 to 25° C., optionally about 21 to 23° C., optionally about 22° C.; and/or (ii) c) is performed for a duration of 5 to 120 minutes, optionally 5 to 65 minutes, optionally 10 to 60 minutes, optionally 10 to 50 minutes, optionally 10 to 40 minutes, optionally 10 to 30 minutes, optionally 10 to 20 minutes; and/or (iii) the oxidizing agent is present in an amount of 0.01 to 0.5 molar equivalents, optionally 0.01 to 0.3 molar equivalents, optionally 0.04 to 0.3 molar equivalents, optionally 0.04 to 0.1, based on the molar amount of disaccharide repeating units of the glycerol-modified hyaluronic acid; and/or (iv) said glycerol-modified hyaluronic acid is present in an amount of 2 to 50 g/L, optionally 2 to 40 g/L, optionally 3 to 38 g/L, optionally 4 to 36 g/L.

5. A modified hyaluronic acid derivative obtained by a method comprising:

a) providing a glycerol-modified hyaluronic acid, wherein a $—CH_2—OH$ group of at least one N-acetyl-D-glucosamine unit is modified into a group of the following formula $—CH_2—O—CH_2—CHOH—CH_2OH$;

b) dissolving the glycerol-modified hyaluronic acid in an aqueous medium to obtain solubilized glycerol-modified hyaluronic acid; and c) reacting said solubilized glycerol-modified hyaluronic acid with an oxidizing agent, optionally a periodate, optionally sodium periodate, to convert at least a part of said $—CH_2—O—CH_2—CHOH—CH_2OH$ groups into aldehyde groups having the formula $—CH_2—O—CH_2—CHO$, thereby obtaining a modified hyaluronic acid derivative, wherein c) is performed for a duration of 5 to 65 minutes, and wherein the degree of modification is 2.0% to 6.9%, the degree of modification being defined as the number of $—CH_2—O—CH_2—CHO$ groups divided by the total number of N-acetyl-D-glucosamine units present in the modified hyaluronic acid derivative; wherein the number of aldehyde groups having the structure $—CH_2—O—CH_2—CHO$ of the at least one N-acetyl-D-glucosamine unit divided by the total number of aldehyde groups present in the modified hyaluronic acid derivative is from 0.95 to 1, wherein the modified hyaluronic acid derivative has a weight average molecular weight of 0.4 MDa to 1.3 MDa, and wherein the modified hyaluronic acid derivative comprises at least one disaccharide unit of the following structure

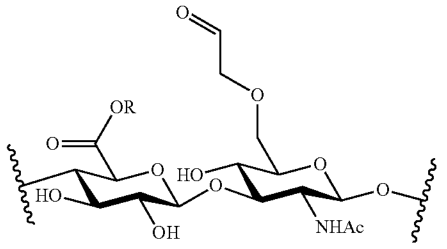

wherein Ac denotes $—C(O)CH_3$ and R is selected from the group consisting of hydrogen, an alkali metal ion and an alkaline earth metal ion, and further comprises at least one disaccharide unit of the following structure

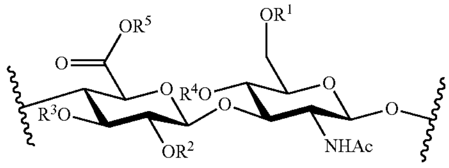

wherein Ac denotes $—C(O)CH_3$, $R^1$, $R^2$, $R^3$ and $R^4$ are independently selected from the group consisting of H and $—CH_2—CHO$, and $R^5$ is selected from the group consisting of hydrogen, an alkali metal ion, an alkaline earth metal ion, and $—CH_2—CHO$, wherein, at least one of $R^1$, $R^2$, $R^3$, $R^4$ and $R^5$ is $—CH_2—CHO$ and, if $R^1$ is $—CH_2—CHO$, at least one of $R^2$, $R^3$, $R^4$ and $R^5$ is $—CH_2—CHO$.

6. A product comprising the modified hyaluronic acid derivative of claim 1 for in situ formation of a crosslinked hydrogel in aesthetic applications, optionally for treating wrinkles and lines of the skin, including glabellar lines, nasolabial folds, chin folds, marionette lines, jawlines, buccal commissures, perioral wrinkles and crow's feet, cutaneous depressions, scars, temples, subdermal support of the brows, malar and buccal fat pads, tear troughs, nose, lips, cheeks, chin, perioral region, infraorbital region, and/or facial asymmetries.

7. A product comprising the modified hyaluronic acid derivative of claim 1 for formation of a pre-formed crosslinked hydrogel.

8. A method for treatment of stress urinary incontinence, vaginal dryness, vesico-ureteral reflux, vocal fold insufficiency, and/or vocal fold medialization comprising injecting the modified hyaluronic acid derivative of claim 1 into a subject in need thereof and in situ formation of a crosslinked hydrogel.

9. The product of claim 6, wherein the modified hyaluronic acid derivative is used together with a second polysaccharide derivative, which comprises one or more nucleophilic functional groups capable of forming a covalent bond with one or more aldehyde groups of the modified hyaluronic acid derivative, wherein the second polysaccharide is optionally a hyaluronic acid derivative and said nucleophilic functional group is optionally a hydrazide functional group, and wherein the second polysaccharide is optionally a hyaluronic acid derivative comprising at least one disaccharide unit having the following structure:

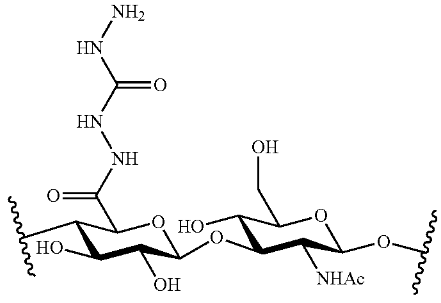, wherein Ac denotes —$C(O)CH_3$.

10. The product of claim 9, wherein (i) an aldehyde group of the modified HA derivative and a nucleophilic functional group of the second polysaccharide derivative spontaneously form a covalent bond upon co-injecting the modified hyaluronic acid derivative and the second polysaccharide derivative to a target site in the body of a subject, thereby forming a crosslinked hydrogel at the target site, or (ii) an aldehyde group of the modified HA derivative and a nucleophilic functional group of the second polysaccharide derivative spontaneously form a covalent bond upon contacting the modified hyaluronic acid derivative and the second polysaccharide derivative, wherein optionally the modified HA derivative and the second polysaccharide derivative are present in a buffer medium, optionally a physiological buffer medium.

11. A crosslinked hydrogel obtained by contacting the modified hyaluronic acid derivative of claim 1 and a second polysaccharide derivative, wherein the crosslinked hydrogel optionally comprises the following structural unit:

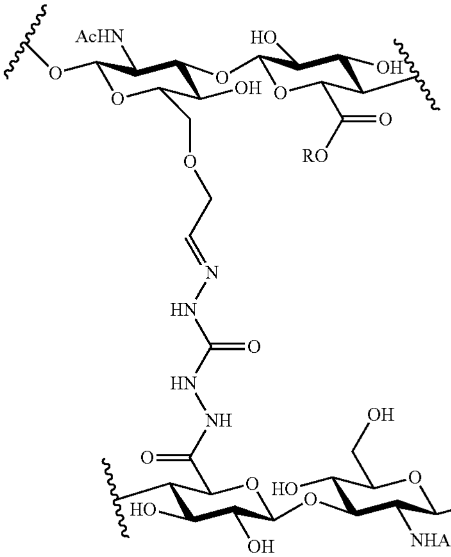

wherein "Ac" denotes —$C(O)CH_3$ and R is selected from hydrogen, an alkali metal ion, optionally Na, and an alkaline earth metal ion.

12. The crosslinked hydrogel according to claim 11, wherein said contacting is performed in situ.

13. The crosslinked hydrogel according to claim 11, wherein said contacting is performed in vitro, wherein said contacting is optionally performed in a buffer, optionally a physiological buffer.

14. A method, optionally an aesthetic method, of preparing a crosslinked hydrogel, the method comprising:

a) providing a first precursor solution comprising the modified hyaluronic acid derivative of claim 1 and, separately thereof, a second precursor solution comprising a second polysaccharide derivative;

b) mixing the first precursor solution and the second precursor solution into an in situ crosslinkable mixture; and c) injecting the in situ crosslinkable mixture to a target site in the body of a patient to form a crosslinked gel at the target site.

15. The method of claim 14, wherein in a) the first precursor solution and the second precursor solution are present in different barrels of a multi-barrel syringe and mixing of b) occurs during extrusion from said multi-barrel syringe.

16. A method of preparing a crosslinked hydrogel, the method comprising:

a) providing a buffer, optionally a physiological buffer;

b) adding the modified hyaluronic acid derivative of claim 1 and adding a second polysaccharide derivative to the buffer, and optionally adding uncrosslinked polysaccharide, optionally hyaluronic acid, to the buffer;

c) crosslinking the modified hyaluronic acid derivative and the second polysaccharide derivative in the buffer to thereby prepare a crosslinked hydrogel;

d) optionally adding uncrosslinked polysaccharide to the crosslinked hydrogel obtained in c);

e) optionally sieving and degassing the hydrogel obtained in c) or d);

f) optionally filling the hydrogel obtained in c), d), or e) in a container, optionally a syringe, optionally a ready-to-use syringe; and g) optionally sterilizing the container comprising the gel obtained in f).

17. A kit for in situ formation of a crosslinked hydrogel, comprising (i) a first container containing a first precursor solution comprising the modified hyaluronic acid derivative of claim 1 and (ii) a second container containing a second precursor solution comprising a second polysaccharide derivative, and optionally, (iii) instructions for use.

* * * * *